United States Patent [19]

Ueno et al.

[11] Patent Number: 5,290,811
[45] Date of Patent: Mar. 1, 1994

[54] USE OF 15-KETO-PROSTAGLANDIN COMPOUND FOR IMPROVEMENT OF ENCEPHALIC FUNCTION

[75] Inventors: Ryuji Ueno; Hiroyoshi Osama; Tomio Oda, all of Hyogo, Japan

[73] Assignee: Kabushiki Kaisha Ueno Seiyaku Oyo Kenkyujo, Osaka, Japan

[21] Appl. No.: 777,595

[22] Filed: Oct. 16, 1991

Related U.S. Application Data

[62] Division of Ser. No. 616,960, Nov. 21, 1990, Pat. No. 5,117,042.

[30] Foreign Application Priority Data

Nov. 22, 1989 [JP] Japan .................. 1-303839
Jan. 17, 1990 [JP] Japan .................... 2-7611
Mar. 30, 1990 [JP] Japan ................... 2-85439

[51] Int. Cl.$^5$ ............................ A61K 31/557
[52] U.S. Cl. .................... 514/530; 514/469; 514/573
[58] Field of Search ............ 514/530, 573, 469

[56] References Cited

U.S. PATENT DOCUMENTS 5,073,569 12/1991 Ueno ........................... 514/530
5,106,809 11/1992 Ueno ........................... 514/530

FOREIGN PATENT DOCUMENTS 0281239 1/1988 European Pat. Off. .
0284180 1/1988 European Pat. Off. .
0289349 4/1988 European Pat. Off. .
0292177 5/1988 European Pat. Off. .
 281239 9/1988 European Pat. Off. ............ 560/121
0308135 9/1988 European Pat. Off. .
0310305 9/1988 European Pat. Off. .
 292177 11/1988 European Pat. Off. ............ 560/121
0342003 5/1989 European Pat. Off. .
0343904 5/1989 European Pat. Off. .
0345951 5/1989 European Pat. Off. .

Primary Examiner—Robert Gerstl
Attorney, Agent, or Firm—Sughrue, Mion, Zinn, Macpeak & Seas

[57] ABSTRACT

A method of treatment for improving encephalic function which comprises administering, to a subject in need of such treatment, a 15-keto-prostaglandin compound in an amount effective for improvement of encephalic function.

30 Claims, No Drawings

USE OF 15-KETO-PROSTAGLANDIN COMPOUND FOR IMPROVEMENT OF ENCEPHALIC FUNCTION

This is a division of application No. 07/616,960 filed Nov. 21, 1990, now U.S. Pat. No. 5,117,042.

BACKGROUND OF THE INVENTION

Field of the Invention

The present invention relates to a use of 15-keto-prostaglandin compound for improvement of encephalic function.

Prostaglandins (hereinafter, prostaglandin is referred to as PG) are members of a class of organic carboxylic acid that are contained in human and most other mammalian tissues or organs and that exhibit a wide range of physiological activities. Naturally occurring PGs possess as a common structural feature the prostanoic acid skeleton:

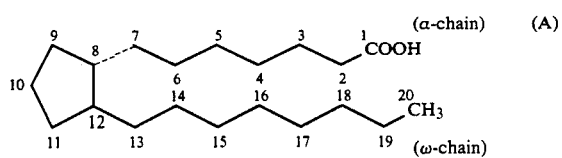

Some of synthetic analogues have somewhat modified skeletons. The PGs are classified based on the structural feature of five-membered ring moiety into PGAs, PGBs, PGCs, PGDs, PGEs, PGFs, PGGs, PGHs and PGJs, while PGIs have an different skeleton, shown below, formed by cyclization between the α-chain and the five-membered ring.

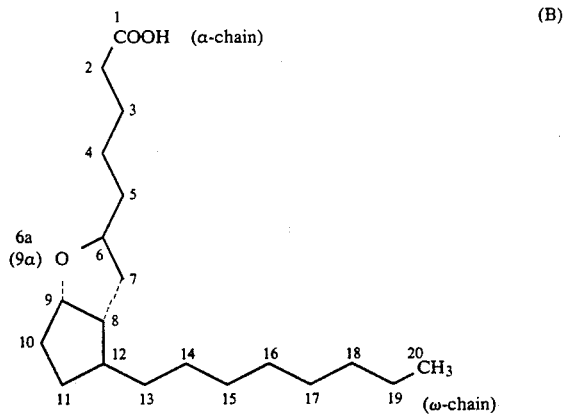

These are further classified based on the presence or absence of unsaturation and oxidation in the chain moiety as:

Subscript 1—13,14-unsaturated-15-OH
Subscript 2—5,6- and 13,14-diunsaturated-15-OH
Subscript 3—5,6- 13,14- and 17,18-triunsaturated-15-OH Further, PGFs are sub-classified according to the configuration of hydroxy groups at 9-position into
α (hydroxy group being in alpha configuration) and
β (hydroxy group being in beta configuration).

Background Information

JP-A-58-164512 discloses that 15-cycloalkyl-6-oxo-$PGE_1$s, 15-cycloalkyl-$PGI_1$s and $PGI_2$s, 15-cycloalkyl-6,9α-nitrilo-$PGI_1$s, and 15-cycloalkyl-6,9α-thio-$PGI_1$s and -$PGI_2$s have a protective effect to cell disorder including cerebral vascular disorder. JP-A-58-203911 discloses that some 6-oxo-$PGE_1$s and $PGI_1$s having one or two methyl substituents on 15,16,17 and/or 20 positions and defined 15-cyclopentyl-$PGI_1$s have a protective effect to cell disorder. JP-A-59-73522 discloses that some $PGD_2$- or $PGE_1$ derivatives can be used as a treating agent for hypoxia of cerebral nerve cells. Further, carbacyclin (also known as 9(O)-methanoprostacyclin or 9(O)-methano-$PGI_2$), which is a synthetic PG derivative having a methylene group in place of the oxygen at position 6a(9α) of $PGI_2$, is known to have an action of inhibiting platelet aggregation. Also, compound having a nitrogen in place of the oxgen at position 6a(9α) and a sulfur in place of the methylene at position 5 of $PGI_2$ (i.e. 9-deoxy-9α,6-nitrilo-5-thia-$PGF_{1α}$) is known. These compounds, however, do not fall within the category of 15-keto-PGs or derivatives thereof.

EP-A-0310305 discloses that 15-keto-PGEs can be used as a cathartic.

PGEs having an oxo group at position 6 and two fluorine atoms at position 5 have also been known (JP-A-32054/1990) which have been described as compounds having actions reducing gastro-juice and preventing stress ulcer. Further, compounds having an oxo group in place of hydroxy group at position 15 and derivatives of these compounds have been known as compounds having anti-ulcer and uterine contracting actions etc. but little intestine contracting action. While the fact that a single compound simultaneously has a plurality of actions may seem to be advantageous, it is also to be noted that in some cases the presence of actions other than those useful in confronted treatment is rather undesirable and seemed to be disadvantageous as having side-effects. Accordingly, a compounds having only the desired action are advantageous from such viewpoint.

Among various causes possible for the deterioration of cerebral function, the local disorder of cerebral vascular kinetics due to ischemic lesion, hemorrhagic lesion or edemstous hydrocephalus and the diffuse disorder due to compressive lesion may be mentioned. Another cause may be the secondary disorder of encephalic metabolism.

In order to treat these disorders, two factors should be considered, i.e. improvement of the cerebral circulation and that of the basic activity of cerebral cells. Accordingly, there is a continuous need for a medicament having both the improving activity.

After an extensive study on the biological activity of 15-keto-PGs, the present inventor discovered that 15-keto-PGs have excellent encephalic metabolism activating action, encephalic function protecting action and encephalic blood circulation improving action, and therefore can be used for improvement of encephalic function.

SUMMARY OF THE INVENTION

In the first aspect, the present invention provides a method of treatment for improving encephalic function which comprises administering, to a subject in need of such treatment, a 15-keto-prostaglandin compound in an amount effective for improvement of encephalic function.

In the second aspect, the present invention provides a use of 15-keto-prostaglandin compound for the manufacture of a medicament for improving encephalic action.

In the third aspect, the present invention provides a pharmaceutical composition for improving encephalic action comprising 15-keto-prostaglandin compound in association with a pharmaceutically acceptable carrier, diluent or excipient.

DETAILED DESCRIPTION OF THE INVENTION

As used herein, the expression "improvement of encephalic function" is intended to include improvement of any conditions comprising or associated with ischemic lesion, hemorrhagic lesion, or local or propagated pressure lesion due to edema or hydrocephalia, and further, improvement of any conditions comprising or associated with disorders of cerebral metabolism secondarily induced by disorders of cerebral circulation kinetics. Examples of such conditions include tansient ischemic attack syndrome (TIA syndrome), ischemic cerebrovascular disorder, atheroscleorotic thrombosis, atherothrombotic lesion of internal carotid artery (including branch), cerebral infarction, cerebral embolism, intracerebral bleeding, subarachnoid hemorrhage, hypertensive encephalopathy, abnormal cerebrovascular network in cerebral basal region, obstruction of cerebral vein or venous sinus, systemic hypotension, anoxic ischemic encephalopathy, traumatic cerebrovascular obstruction, commotion of brain, cerebral contusion, epidural hematoma, subdural hematoma, cerebrovascular spasm, and further, cerebrovascular disorders such as intracerebral bleeding, cerebral infarction, subarachnoid hemorrhage, hypertensive encephalopathy etc., encephalitis, brain tumor, head injury such as cerebrovascular obstruction, commotion of brain, cerebral contusion, epidural hepatoma, subdural hepatoma etc., psychosis, metabolic disorder, drug intoxication induced by alcohol, drug, narcotic etc., poison intoxication induced by heavy metal, organic solvent, toxic gas, biological poison etc., disturbance of consciousness due to physical disorder etc., and secondary disease of the above disorders such as disturbance of memory, aprosexia, hyperkinesis, speech disorder, mental retardation etc., amnesia, senile dementia Alzheimer's disease etc.

The term "treatment" includes any treatment, such as management, of a disease, including prevention, therapy, alleviation of symptom, arrest of development and/or alleviation of development of the disease.

The term "15-keto-prostaglandin compound", referred to as 15-keto-PG compound, includes any prostaglandin derivatives which have an oxo group in place of the hydroxy group at position 15 of the prostanoic acid nucleus irrespective of the presence or absence of the double bond between 13- and 14-positions.

Further, the term "prostaglandin I compound" includes any compound formed by cyclizing between positions 6 and 9 of the prostanoic acid with the interposition of one atom (e.g. C,O,S,N, etc.), derivatives irrespective of the number of double bond, the presence of other substituent and any change in chain moieties.

Nomenclature

Nomenclature of 15-keto-PG compounds herein uses the numbering system of prostanoic acid represented in the formulas (A) and (B) shown above.

While the formulas (A) and (B) show basic skeletons having twenty carbon atoms, the 15-keto-PG compounds used in the present invention are not limited to those having the same number of carbon atoms. The carbon atoms in the Formulas (A) and (B) are numbered 2 to 7 on the α-chain (or 2 to 5 on the α-chain and 6,6a (or 9α) and 7 on the ring formed in the formula (B)) starting from the α-carbon atom adjacent to the carboxylic carbon atom which is numbered 1 and towards the five-membered ring, 8 to 12 on the ring common in the formulas (A) and (B) starting from the carbon atom on which the α-chain in the formula (A) is attached or the corresponding carbon atom in the formula (B), and 13 to 20 on the ω-chain starting from the carbon atom adjacent of the ring. When number of carbon atoms is decreased in the α-chain, the number is deleted in order starting from 2-position and when number of carbon atoms is increased in the α-chain, compounds are named as substituted derivatives having respective substituents at 1-position in place of carboxy group (C-1). Similarly, when number of carbon atoms is decreased in the ω-chain, the number is deleted in order starting from 20-position and when number of carbon atoms is increased in the ω-chain, compounds are named as substituted derivatives having respective substituents at 20 position. Stereochemistry of compounds is the same as that of the above formulas (A) and (B) unless otherwise specified.

Thus, 15-keto-PGs having 10 carbon atoms in the ω-chain is nominated as 15-keto-20-ethyl-PGs. In another example, a $PGI_2$ compound saturated between positions 13 and 14, having an oxo group in place of the hydroxy group at position 15 and a carbon atom (as $CH_2$) in place of oxgen atom at position 6a(9α) is nominated as 13, 14-dihydro-15-keto-6a-carba-$PGI_2$ (or 13,14-dihydro-15-keto-9(O)-methano-$PGI_2$).

The above formula expresses a specific configuration which is most typical one, and in this specification compounds having such a configuration are expressed without any specific indication about it.

Although PGDs, PGEs, PGFs and PGIs generally refer to compounds having a hydroxy group at position 9 and/or 11 of the prostanoic acid nucleus, the 15-keto-prostaglandin compounds in the present invention are extended to include compounds having another group at position 9 and/or 11. Such compounds are named as 9-dehydroxy-9-substituted or 11-dehydroxy-11-substituted compounds.

As stated above, nomenclature of 15-keto-PG compounds is based upon the prostanoic acid. These compounds, however, can also be named according to the IUPAC naming system. For example, 13,14-dihydro-15-keto-16R,S-fluoro-$PGE_2$ is (Z)-7-{(1R,2R,3R)-3-hydroxy-2-[(4R,S)-4-fluoro-3-oxo-octyl]-5-oxo-cyclopentyl}-ept-5-enic acid. 13,14-dihydro-15-keto-16,16-difluoro-$PGE_2$ is (Z)-7-[(1R,2R,3R)-2-(4,4-difluoro-3-oxo-octyl)-3-hydroxy-5-oxo-cyclopentyl]-hept-5-enoic acid. 13,14-dihydro-15-keto-20-ethyl-11-dehyroxy-11R-methyl-$PGE_2$ methyl ester is methyl 7-{(1R,2S,3S)-3-methyl-2-[3-oxo-decyl]-5-oxo-cyclopentyl}-hept-5-enoate. 13,14-dihydro-6,15-diketo-19-methyl-$PGE_1$ ethyl ester is ethyl 7-{(1R,2S,3S)-3-hydroxy-2-(7-methyl-3-oxo-octyl)-5-oxo-cyclopentyl}-6-oxo-heptanate.

Preferred Compounds

The 15-keto-PG compounds used in the present invention may be any derivatives of PG in so far as they have an oxo group at position 15 in place of the hydroxy group, and may have a single bond (15-keto-PG subscript 1 compounds), a double bond (15-keto-PG subscript 2 compounds) between positions 5 and 6, or two double bonds (15-keto-PG subscript 3 compounds) between positions 5 and 6, 13 and 14 as well as 17 and 18. Also 13,14-dihydro compounds are included.

Typical examples of the compounds used in the present invention are 15-keto-PGX wherein PGX is any PG selected from PGA, PGB, PGC, PGD, PGE, PGF, PGG, PGH, PGI and PGJ, 13,14-dihydro-15-keto-PGX and so on as well as their derivatives.

Said derivatives include esters at the carboxy group at the alpha chain, pharmaceutically acceptable salts, unsaturated derivatives having a double bond or a triple bond between positions 2 and 3 or positions 5 and 6, respectively, substituted derivatives having substituent(s) on carbon atom(s) at position 3, 5, 6, 16, 17, 19 and/or 20 and compounds having lower alkyl or a hydroxy (lower) alkyl group at position 9 and/or 11 in place of the hydroxy group.

Examples of substituents presents in preferred compounds are as follow: Substituents on the carbon atom at position 3, 5, 17 and/or 19 include lower alkyl, for example, $C_{1-4}$ alkyl, especially methyl and ethyl. Substituents on the carbon atom at position 16 include lower alkyl such as methyl, ethyl etc., hydroxy and halogen atom such as chlorine, fluorine, aryloxy such as trifluoromethylphenoxy etc. Substituents on the carbon atom at position 17 include halogen atom such as chlorine, fluorine etc. Substituents on the carbon atom at position 20 include saturated and unsaturated lower alkyl such as $C_{1-4}$ alkyl, lower alkoxy such as $C_{1-4}$ alkoxy and lower alkoxy (lower) alkyl such as $C_{1-4}$ alkoxy-$C_{1-4}$ alkyl. Substituents on the carbon atom at position 5 include halogen atom such as chlorine, fluorine etc. Substituents on the carbon atom at position 6 include oxo group forming carboxyl. Stereochemistry of PGs having hydroxy, lower alkyl or lower (hydroxy) alkyl substituent on the carbon atom at position 9 and/or 11 may be alpha, beta or mixture thereof.

Said derivatives may have alkoxy, phenoxy or phenyl group at the end of the omega chain where the chain is shorter than the natural PGs.

Especially preferred compounds are those having a lower alkyl such as methyl, ethyl etc., a halogen atom such as chloro, fluoro etc. at position 16, those having a lower alkyl such as methyl, ethyl etc. at position 19, those having halogen atom such as chlorine, fluorine etc. at position 5, those having an oxo at position 6, those having a lower alkyl such as methyl, ethyl etc. at position 20, and those having phenyl or phenoxy which are optionally substituted with halogen or haloalkyl at position 16 in place of the rest of chain.

A group of preferred compounds used in the present invention has the formula

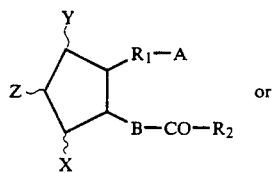

or

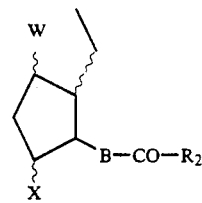

wherein X and Y are hydrogen, hydroxy, halo, lower alkyl, hydroxy(lower)alkyl, or oxo with the proviso that at least one of X and Y is other than hydrogen and the five-membered ring may have at least one double bond, Z is hydrogen or halo, A is —$CH_2OH$, —$COCH_2OH$, —COOH or its functional derivative, B is —$CH_2$—$CH_2$—, —CH=CH— or —C≡C—, W is oxygen atom or carbon atom, $R_1$ is bivalent saturated or unsaturated, lower or medium aliphatic hydrocarbon residue, which is unsubstituted or substituted with halogen, oxo or aryl, $R_2$ is saturated or unsaturated, lower or medium alphatic hydrocarbon residue which is unsubstituted or substituted with halo, hydroxy, oxo, lower alkoxy, lower alkanoyloxy, cyclo(lower)alkyl, aryl or aryloxy, with the proviso that the third carbon atom form the five-membered ring is substituted with an oxo group.

Among the compounds of the above formula, the compounds represented by the following formula are novel and form also part of the present invention.

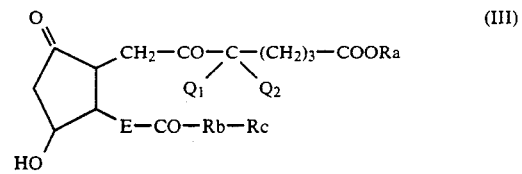

wherein $Q_1$ is halogen, $Q_2$ is hydrogen or halogen, E is —$CH_2$—$CH_2$— or —CH=CH—, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, monocyclic aryl which is unsubstituted or substituted with halogen or halo(lower) alkyl, or monocyclic aryloxy which is unsubstituted or substituted with halogen or halo(lower) alkyl or a pharmaceutically acceptable salts in case of Ra is hydrogen.

Since they have a specific profile that they have only part of action (e.g. an action improving encephalic function) of PGE while lacking the rest of action, they are useful as selective PGE-like agent.

In the above formula, the term "unsaturated" in the definitions for $R_1$ and $R_2$ is intended to include at least one and optionally more than one double bond and/or triple bond isolatedly, separately or serially present between carbon atoms of main and/or side chain. According to usual nomenclature, an unsaturation between two serial positions is represented by denoting younger number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarboyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, preferably 1 to 5 and more preferable 1 to 4 carbon atoms, such as methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "lower alkylene" refers to the group obtainable by removing a hydrogen atom from the lower alkyl group as defined above and includes e.g. methylene, ethylene, propylene, tetramethylene, 2-methyltetramethylene, pentamethylene, hexamethylene etc.

The term "halo(lower) alkyl" refers to lower alkyl group as defined above which is substituted with at least one and preferably 1 to 3 halogen atoms as defined above and includes e.g. chloromethyl, bromomethyl, fluoromethyl, trifluoromethyl, 1,2-dichloromethyl, 1,2,2-trichloroethyl, chloropropyl, chlorobutyl, chloropentyl, chlorohexyl etc.

The term "hydroxy(lower)alkyl" refers to alkyl as defined above and substituted with at least one hydroxy group, such as hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower) alkyl wherein halo and lower alkyl being as defined above.

The term "aryloxy" refers to a group of the formula: ArO— wherein Ar is aryl as defined above.

The term "monocyclic aryl" includes phenyl unsubstituted or substituted with lower alkyl substituents, e.g. phenyl, tolyl, xylyl, cumenyl etc.

The term "monocyclic aryloxy" refers to a group of the formula: m.Aro-wherein mAr is monocyclic aryl as defined above and includes e.g. phenoxy, tolyloxy, cumenyloxy etc.

The term "functional derivative" of carboxy as A includes salts (preferably pharmaceutically acceptable salts), esters and amides.

Suitable "pharmaceutically acceptable salt" includes conventional non-toxic salt, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkylammonium salt and the like. These salts can be prepared by the conventional process, for example from the corresponding acid and base or by salt interchange.

Examples of the esters are aliphatic esters, for example, $C_{1-6}$ alkyl ester such as methyl ester, ethyl ester, propyl ester, isopropyl ester, butyl ester, isobutyl ester, t-butyl ester, pentyl ester, 1-cyclopropylethyl ester, etc., lower alkenyl ester such as vinyl ester, allyl ester, etc., lower alkynyl ester such as ethynyl ester, propynyl ester, etc., hydroxy(lower) alkyl ester such as hydroxyethyl ester, lower alkoxy(lower)-alkyl ester such as methoxymethyl ester, 1-methoxyethyl ester, etc., and aromatic esters, for example, optionally substituted aryl ester such as phenyl ester, tolyl ester, t-butylphenyl ester, salicyl ester, 3,4-di-methoxyphenyl ester, benzamidophenyl ester etc., aryl(lower)alkyl ester such as benzyl ester, trityl ester, benzhydryl ester, etc. Examples of the amides are mono- or di- lower alkyl amides such as methylamide, ethylamide, dimethylamide, etc., arylamide such as anilide, toluidide, and lower alkyl- or aryl-sulfonylamide such as methylsulfonylamide, ethylsulfonylamide, tolylsulfonylamide etc.

Preferred examples of A include —COOH, —COOCH$_3$, —COOCH$_2$CH$_3$, —COOCH(CH$_3$)$_2$ and —CONHSO$_2$CH$_3$.

Examples of preferred $R_1$ are —(CH$_2$)$_2$—, —(CH$_2$)$_6$—, —CH$_2$CO(CH$_2$)$_2$—, —CH$_2$CH=CH(CH$_2$)$_3$—, —CH$_2$CO(CH$_2$)$_4$—, —(CH$_2$)$_2$CH=CH(CH$_2$)$_2$—, —(CH$_2$)$_4$CH=CH—, —CH$_2$CH=C=CH(CH$_2$)$_2$— etc.

Examples of preferred $R_2$ are —(CH$_2$)$_2$CO(CH$_2$)$_4$—CH$_3$, —(CH$_2$)$_2$CO(CH$_2$)$_4$—COOH, —(CH$_2$)$_2$COC(CH$_3$)$_2$(CH$_2$)$_3$—CH$_3$, —(CH$_2$)$_2$COCH$_2$O-phenyl, —(CH$_2$)$_2$COCH$_2$O-methachlorophenyl, —(CH$_2$)$_2$COCH$_2$O-methatrifluorophenyl, —(CH$_2$)$_2$COCH$_2$O-3-thienyl, —(CH$_2$)$_2$CO(CH$_2$)$_2$-phenyl, —(CH$_2$)$_2$COCH$_2$CH(CH$_3$)(CH$_2$)$_3$CH$_3$, —(CH$_2$)$_2$COC(CH$_3$)$_2$CH$_2$OCH$_2$CH$_3$, —(CH$_2$)$_2$COCH(CH=CH)(CH$_2$)$_3$CH$_3$, —(CH$_2$)$_2$CO-cyclopentyl, —(CH$_2$)$_2$CO-cyclohexyl, —(CH$_2$)$_2$CO(CH$_2$)$_2$-cyclohexyl, —(CH$_2$)$_2$COCH$_2$CH(CH$_3$)(CH$_2$)CH=C(CH$_3$)$_2$, —(CH$_2$)$_2$COCH(CH$_3$)CH$_2$CC=CH, —CH=CHCO(CH$_2$)$_4$—CH$_3$, —CH=CHCOC(CH$_3$)$_2$(CH$_2$)$_3$—CH$_3$, —CH=CHCOCH$_2$O-phenyl, —CH=CHCOCH$_2$O-methachlorophenyl, —CH=CHCOCH$_2$O-methatrifluorophenyl, —CH=CHCOCH$_2$O-3-thienyl, —CH=CHCO(CH$_2$)$_2$-phenyl, —CH=CH-COCH$_2$CH(CH$_3$)(CH$_2$)$_3$CH$_3$, —CH=CH-COC(CH$_3$)$_2$CH$_2$OCH$_2$CH$_3$, —CH=CH-COCH(CH=CH)(CH$_2$)$_3$CH$_3$, —CH=CHCO-cyclopentyl, —CH=CHCO-cyclohexyl, —CH=CH-COCH$_2$CH(CH$_3$)(CH$_2$)$_2$CH=C(CH$_3$)$_2$, —CH=CH-COCH(CH$_3$)CH$_2$CC=CH, —CH=CH-COCH(CH$_3$)(CH$_2$)$_4$CH$_3$ etc.

The configration of the ring and α- and/or ω-chain in the above formulas (I) and (II) may be the same as or different from that in the natural prostaglandins. However, the present invention also include a mixture of a compound having natural configuration and that of unnatural configuration.

Examples of the typical compounds of the present invention are 15-keto-PGs and 13,14-dihydro-15-keto-PGs and their derivatives such as 6-oxo-derivatives, Δ$^2$-derivatives, 3R,S-methyl-derivatives, 5R,S-fluoro-derivatives, 5,5-difluoro-derivatives, 16R,S-methylderivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives, 20-methyl-derivatives, 20-ethyl-derivatives, 19-desmethyl-derivatives and 16-desbutyl-16-phenoxy-derivatives.

In the 15-keto-PG compounds used in the present invention, when the bond between 13- and 14-positions is saturated, a keto-hemiacetal equilibrium may sometimes be formed by the formation of a hemiacetal between the hydroxy group at 11-position and the keto group at 15-position.

When these tautomeric isomers are present, the ratio of the existing isomers will vary depending on the structure of other part of the molecule or the kind of possible substituents and in some cases one of the isomers is predominantly present. The present invention, however, includes both isomers, and while any compound of the invention may be represented by a structure or nomenclature of keto-type, this should be understood as a matter of mere convenience and should not be considered to be intended to exclude the compound in hemiacetal type isomer.

In the present invention, indivisional tautomeric isomers, a mixture thereof, or optical isomers, a mixture thereof, racemic mixture and other isomers such as stereoisomers can be used in the some purpose.

Some of the compounds used in the present invention are novel and may be prepared by the method disclosed in Japanese Patent Publications A-64-52753, A-1-104040, A-1-151519, A-2-131446 etc. Alternatively, these compounds may be prepared by a process analogous to that described herein or to known process.

A practical preparation of the 15-keto compounds involves the following steps; referring to the Synthetic Charts I to III, reaction of the aldehyde (2) prepared by the Collins oxidation of commercially available (−)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein ω-chain is a 13,14-dihydro-15-keto-alkyl group is prepared.

Using the above tetrahydropyranyl ether (7), 6-keto-PGE₁s (15) of which a group constituted with carbon atoms at positions 5, 6 and 7 is

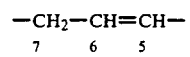

may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at 9-position with NBS or iodine to give the halogenated compound (11), dehydrohalogenation of the compound (11) with, for example, DBU to give the 6-keto compound (13) followed by Jones oxidation and removal of the protecting groups.

Furthermore, PGE₂s (19) of which a group constituted with carbon atoms positions 5, 6 and 7 is

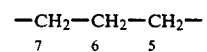

may be prepared in the following steps; as shown in the Synthetic Chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above the tetrahydropyranyl ether (7) as the starting material, the compound having

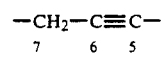

may be prepared by using the same process as that for preparing PGE₂ having —CH₂CH═CH— and subjecting the resultant compound (18) to catalytic reduction for reducing the double bond between the positions 5 and 6 followed by removal of the protective groups.

Synthesis of 5,6-dehydro-PGE₂s having

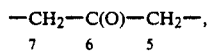

may be carried out by capturing a copper enolate formed by 1,4-addition of a monoalkylcopper complex or a dialkylcopper complex of the following formulae:

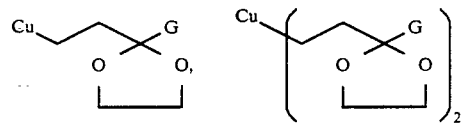

wherein G is alkyl to 4R-t-butyldimethylsilyloxy-2-cyclopenten-1-one with 6-alkoxycarbonyl-1-iodo-2-hexyne or the derivatives.

The 11-β type PGEs can be prepared according to the Synthetic Chart III.

PGE derivatives having methyl group at position 11 in place of hydroxy can be prepared by reacting a dimethyl copper complex with PGA-type compound obtained by subjecting 9-hydroxy-11-tosylate to the Jones oxidation.

Alternatively, they can be prepared by protecting carbonyl of saturated ketone (4) produced by reduced by reducing unsaturated ketone (3), eliminating p-phenylbenzoyl and tosylating the produced alcohol, treating with DBU to form a lactol, introducing the alpha-chain by Wittig reaction, oxidizing the alcohol at 9-position to give PGA-type compound, and reacting the product with dimethyl copper complex in order to introduce a methyl group into position 11 to give 11-methyl-PGE-type compound, which on reduction with e.g. sodium borohydride gives 11-methyl-PGF-type compound. 11-hydroxymethyl-PGE-type compound, is obtained by a benzophenone-sensitized photoaddition of methanol of PGA-type compound, which is reduced with e.g. sodium borohydride to give 11-hydroxymethyl-PGF-type compound. The 16-mono- or 16,16-di-halo type PGEs can be prepared according to the Synthetic Chart IV. The synthetic route for the compounds used in the present invention is not limited to the above one and may vary using different protecting, reducing and/or oxidizating methods.

Furthermore, the novel compounds of the formula III may be prepared by the following process, as summarized in Synthetic Charts V to VII, wherein P1, P2, P3, P4, P5, P6, P7, P8, Pa, Pb, Pc and Pd are protective groups, R'a is lower alkyl and Rb and Rc are the same as above.

Referring to Synthetic Chart V, a protected Corey lactone (40) (commercially available) having a suitable protective group (e.g. 4-phenylbenzoyl) is oxidized (e.g. by Collins oxidation) and the produced aldehyde (41) is reacted with (2-oxoalkyl) phosphonic acid ester having desired R2 and R3 groups to give the compound (42). The oxo group is reduced to form (43), which is converted into (44) by protecting reaction. The acyl group at position 11 is removed to produce (45), to which another protective group (e.g. tetrahydropyramyl) is introduced to give (46). The lactone ring is opened with alkali to form a carboxylic acid which, on esterification, gives (47). A protective group (e.g. tetrahydropyranyl) is introduced into (47) to give (48). After reducing the ester group by a reducing agent (e.g. by isobutylaluminum hydride) into an aldehyde group, the produced compound is reacted with an α-chain introducing agent (f) in the presence of a basic condensing agent (e.g. litium isopropyl amide) to form (49), of which the terminal group in α-chain is deprotected to produce (50). The obtained alcohol is oxidized (e.g. by Collins oxydation) and then esterified to give (51) and the group at position 5 is decarboxylated to afford (52). A protective group is removed by a method according to the nature of said group to form (53), which is reduced (e.g. catalytically) to form (54), which, on oxidation (e.g. by Collins oxidation) of position 15 gives (55). Deprotection of (55) produces (56), which, after protecting position 11 alone, is oxydized (e.g. by Collins oxydation) to give (57). This is deprotected to afford the desired (58). In the above process, when the reduction of (53) to (54) is omitted, an unsaturated compound is obtained. A compound wherein Ra is hydrogen can be obtained by hydrolyzing the compound (58).

The α-chain introducing agent (f) is prepared by a process shown in Synthetic Chart V. Thus, E-caprolactone (a) is ring-opened by an alcohol which can form the carboxy protective group Pa to give (b). The hydroxy group is protected to give (c), which is decarboxylated to (d), halogenated to (e) and then subjected to halogen exchange reaction to afford the compound (f).

In another process referring to Synthetic Chart VI, the protected Corey lactone (40) is converted into the compound (59) by reaction steps similar to that from (1) to (7) in synthetic Chart I. The compound (59) is hydrolyzed by alkali (e.g. sodium or potassium hydroxide) to form the free acid (60), which is esterified (e.g. with diazomethane) to give (61). After protecting the hydroxy group at position 9 giving (62), the ester group is reduced (e.g. by lithium aluminum hydride) to produce an alcohol (63) and newly formed hydroxy group is oxidized (e.g. by Swan oxidation) to an aldehyde (64). The aldehyde is reacted with an α-chain introducing agent (i) in the presence of zinc dust and mercuric chloride under ultrasonic irradiation to produce the compound (65). This is deprotected to form (66) and hydrogenated (e.g. over Pd/C) to afford (67), which is then oxidized in two steps (e.g. swan oxidation and Jone's oxidation), via (68), to give (69). The acid (69) is deprotected either directly to (71) or via ester (70) to (72).

The α-chain introducing agent (i) is prepared by a process shown is synthetic Chart VIII. Thus, the acetylenic alcohol (g) is protected to form (h), which is reacted with difromodifluoromethane to produce (i).

Corresponding other PG compounds can be prepared analogously.

Synthetic Chart I

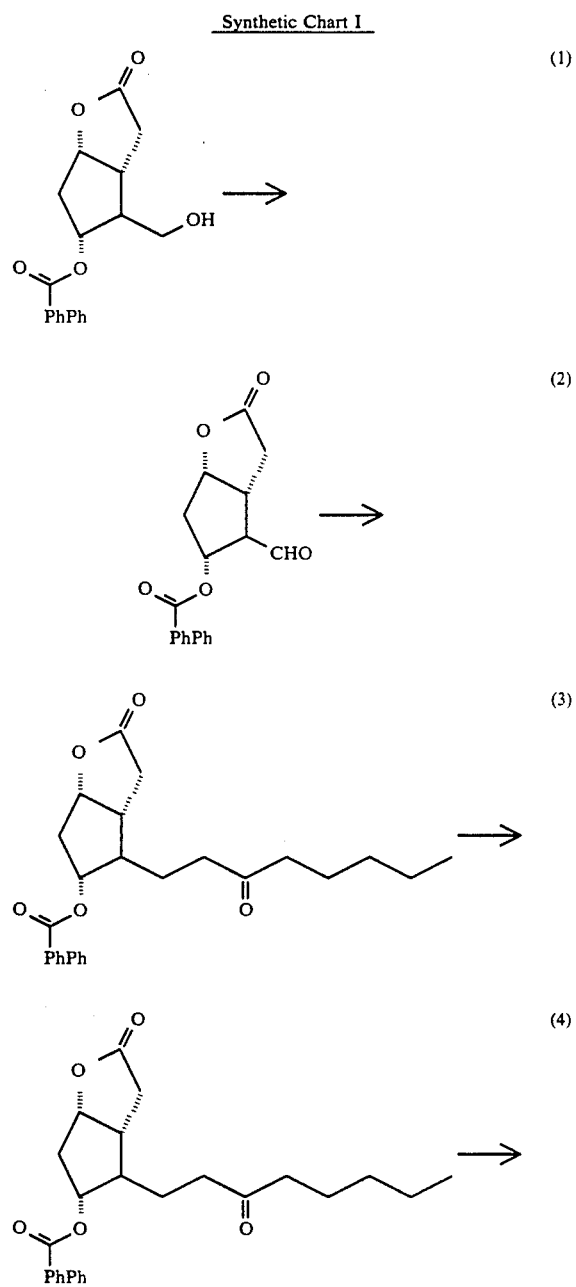

-continued
Synthetic Chart I
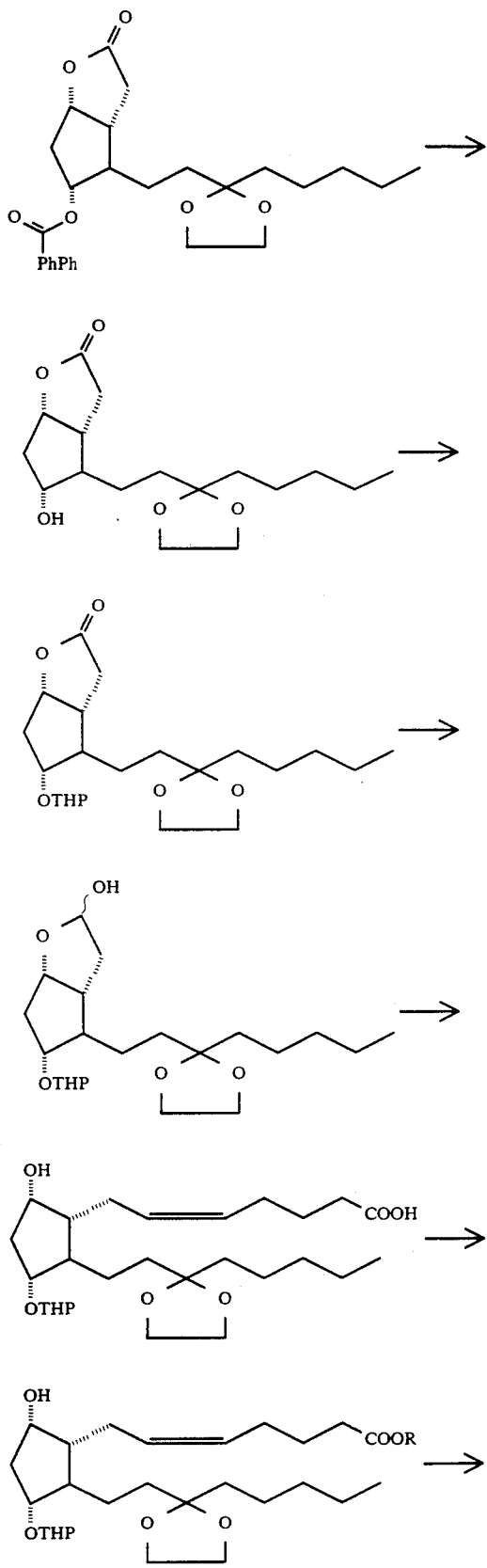
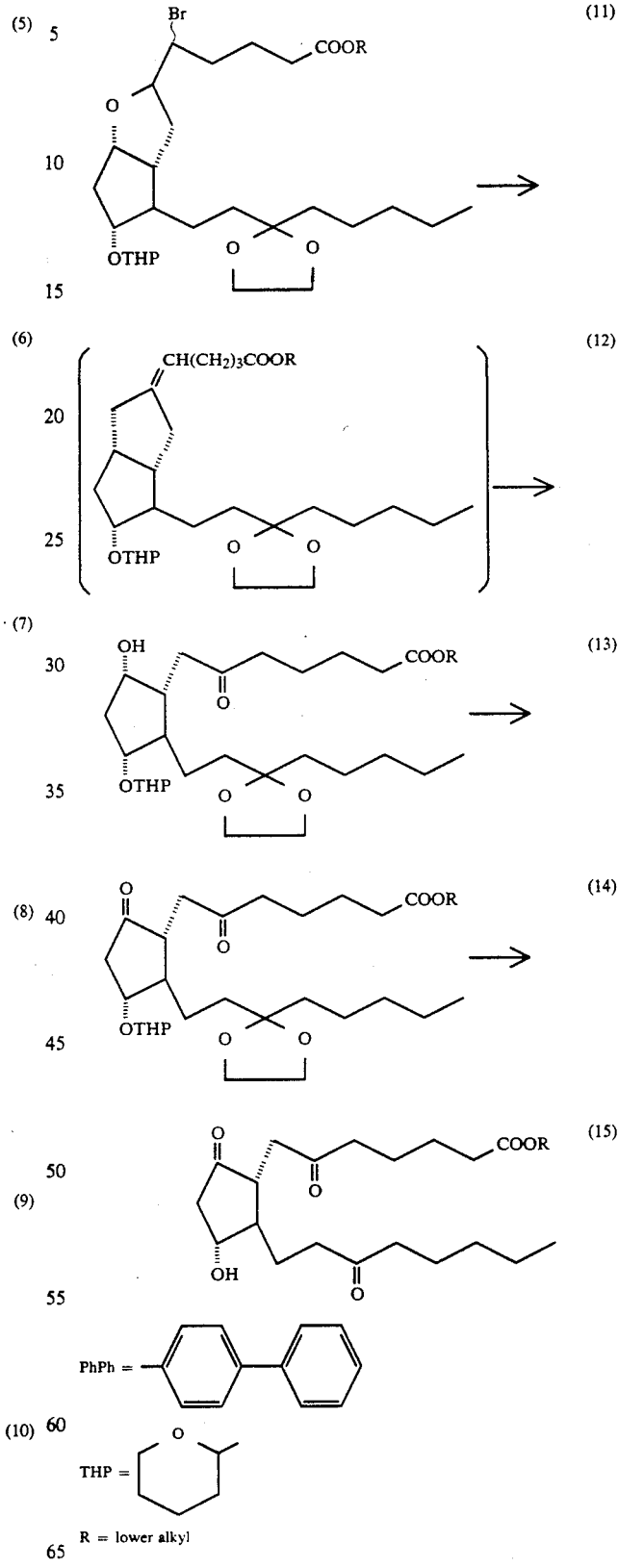

Synthetic Chart II
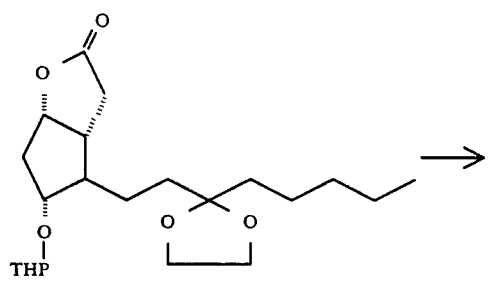 (7)
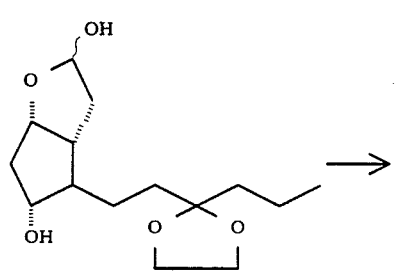 (8)
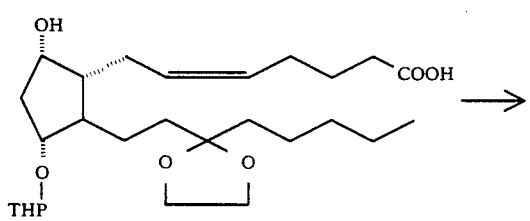 (16)
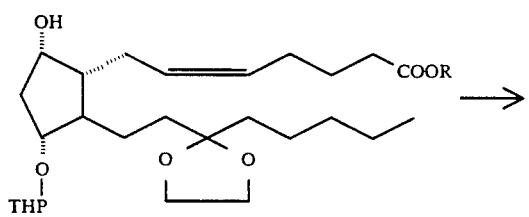 (17)
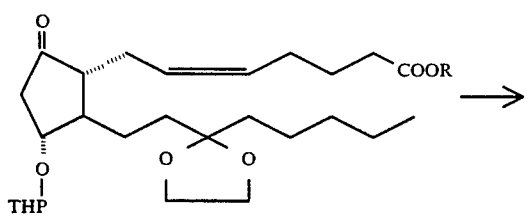 (18)
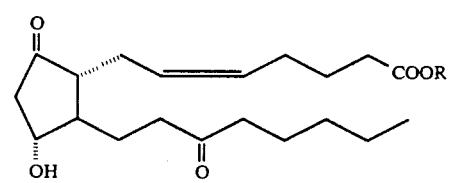 (19)
Synthetic Chart III
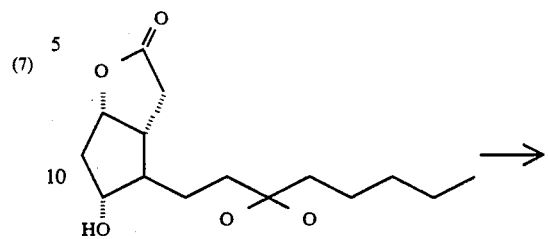 (6)
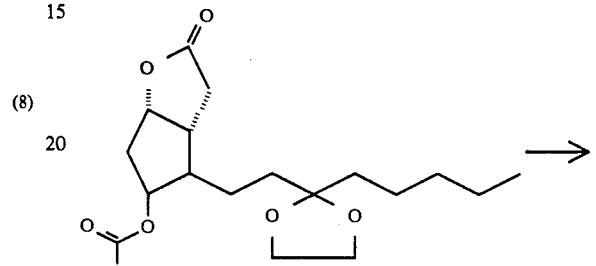 (20)
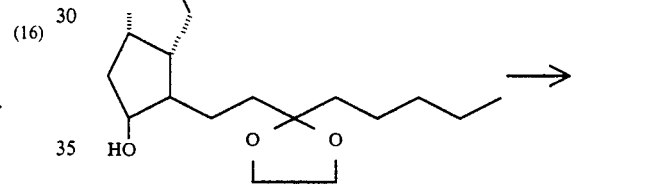 (21)
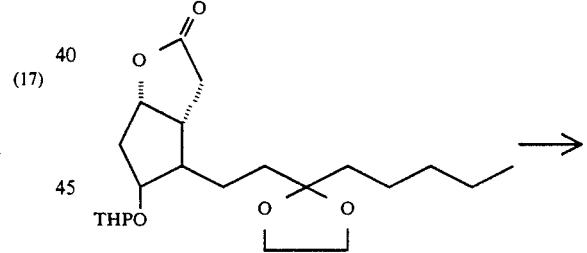 (22)
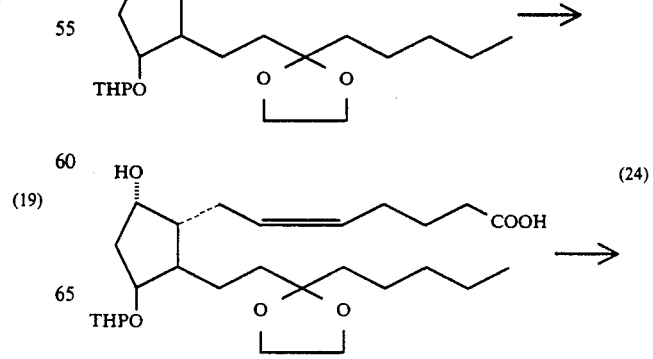
(23)
(24)

-continued
Synthetic Chart III
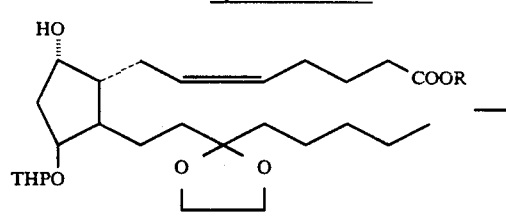 (25)
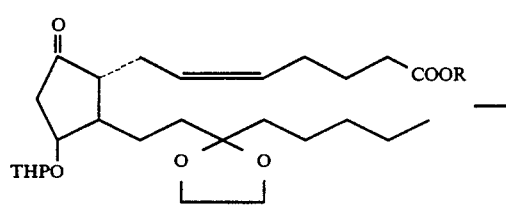 (26)
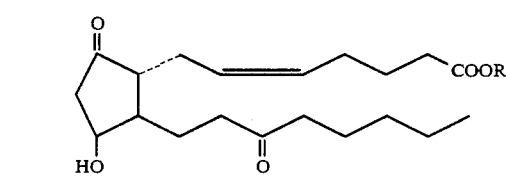 (27)
Synthetic Chart IV
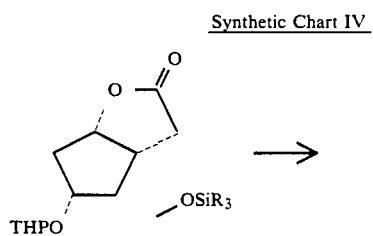 (28)
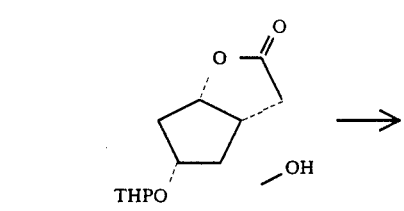 (29)
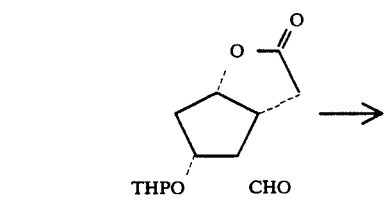 (30)
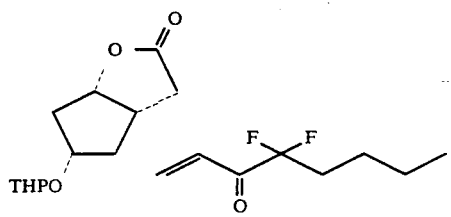 (31)
-continued
Synthetic Chart IV
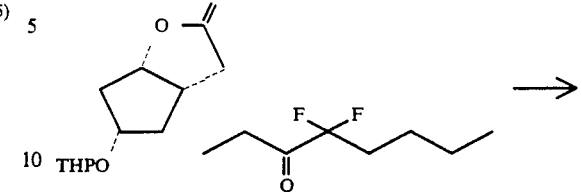 (32)
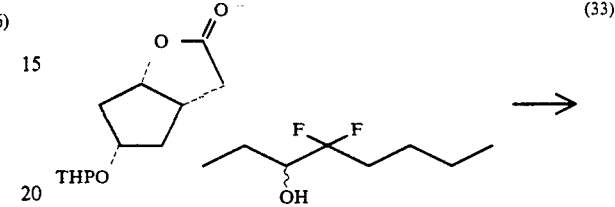 (33)
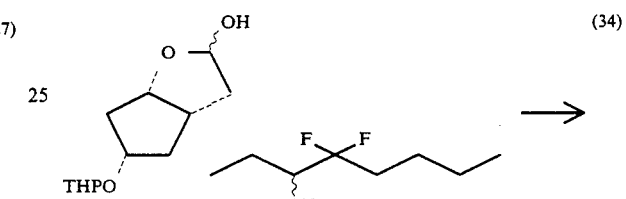 (34)
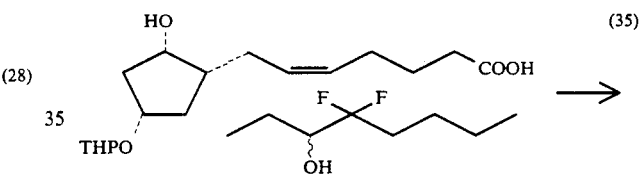 (35)
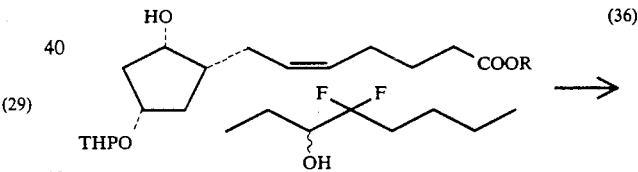 (36)
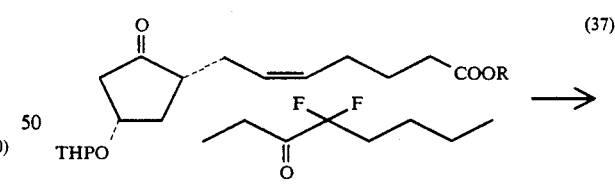 (37)
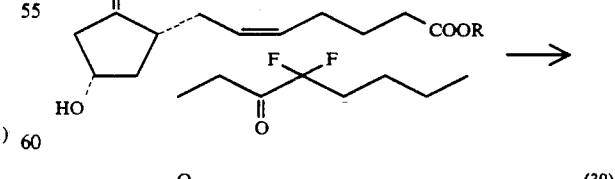 (38)
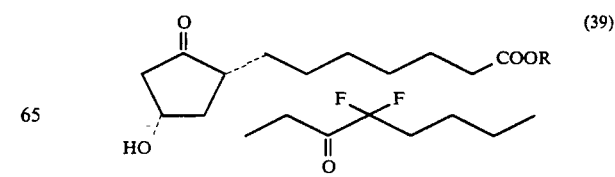 (39)

Synthetic Chart V
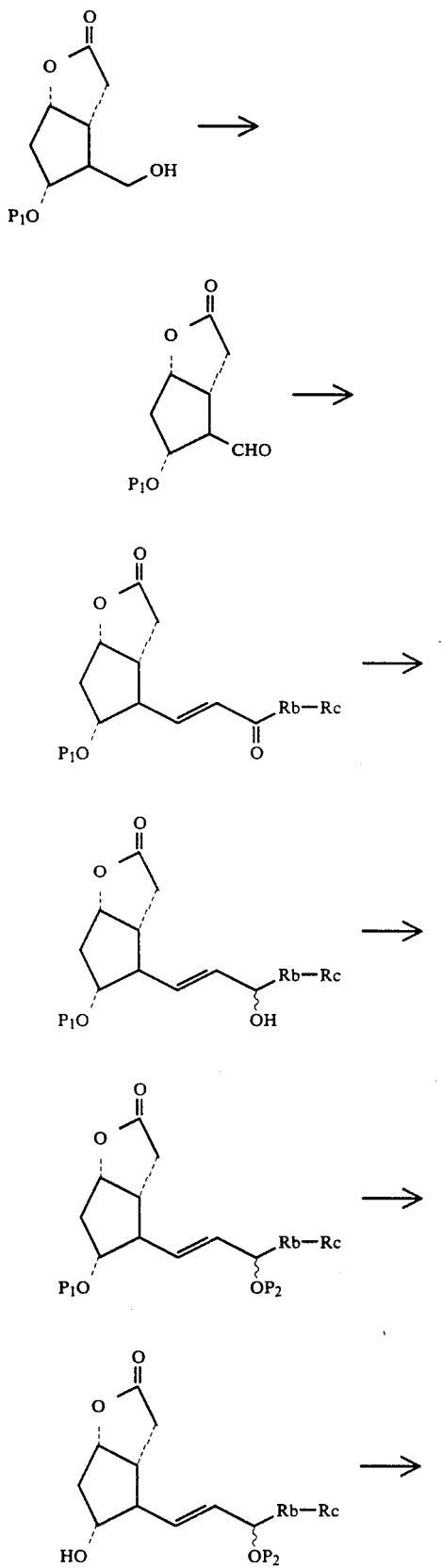
-continued
Synthetic Chart V
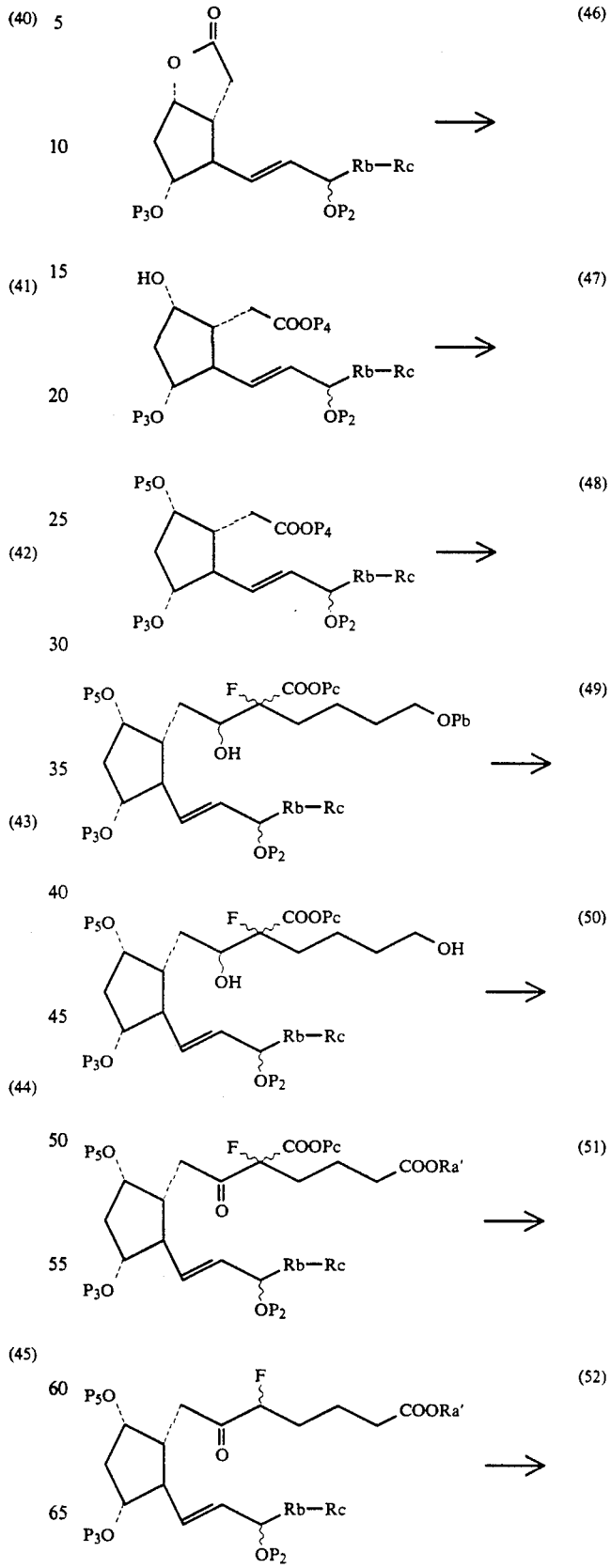

-continued
Synthetic Chart V
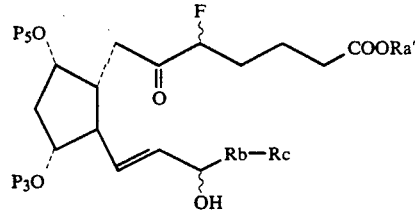
(53)
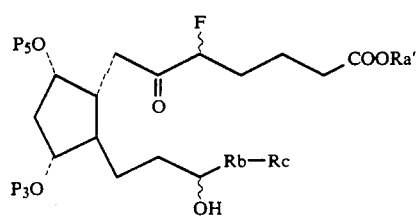
(54)
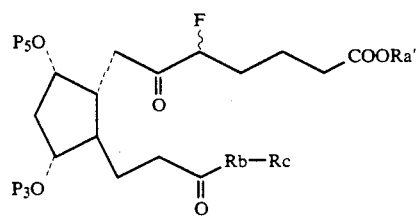
(55)
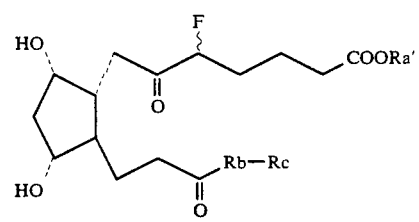
(56)
-continued
Synthetic Chart V
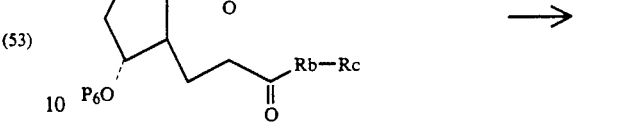
(57)
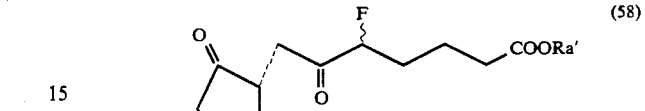
(58)
Synthetic Chart VI
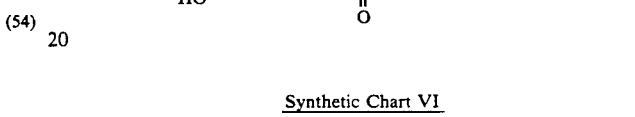
(a)
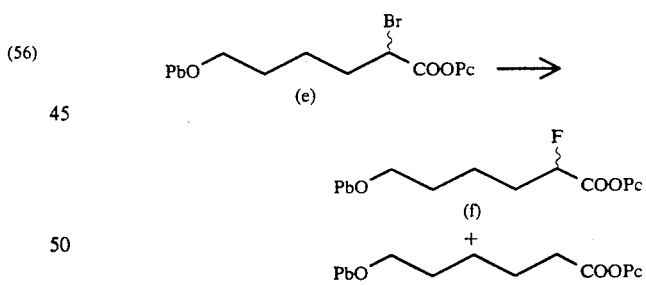

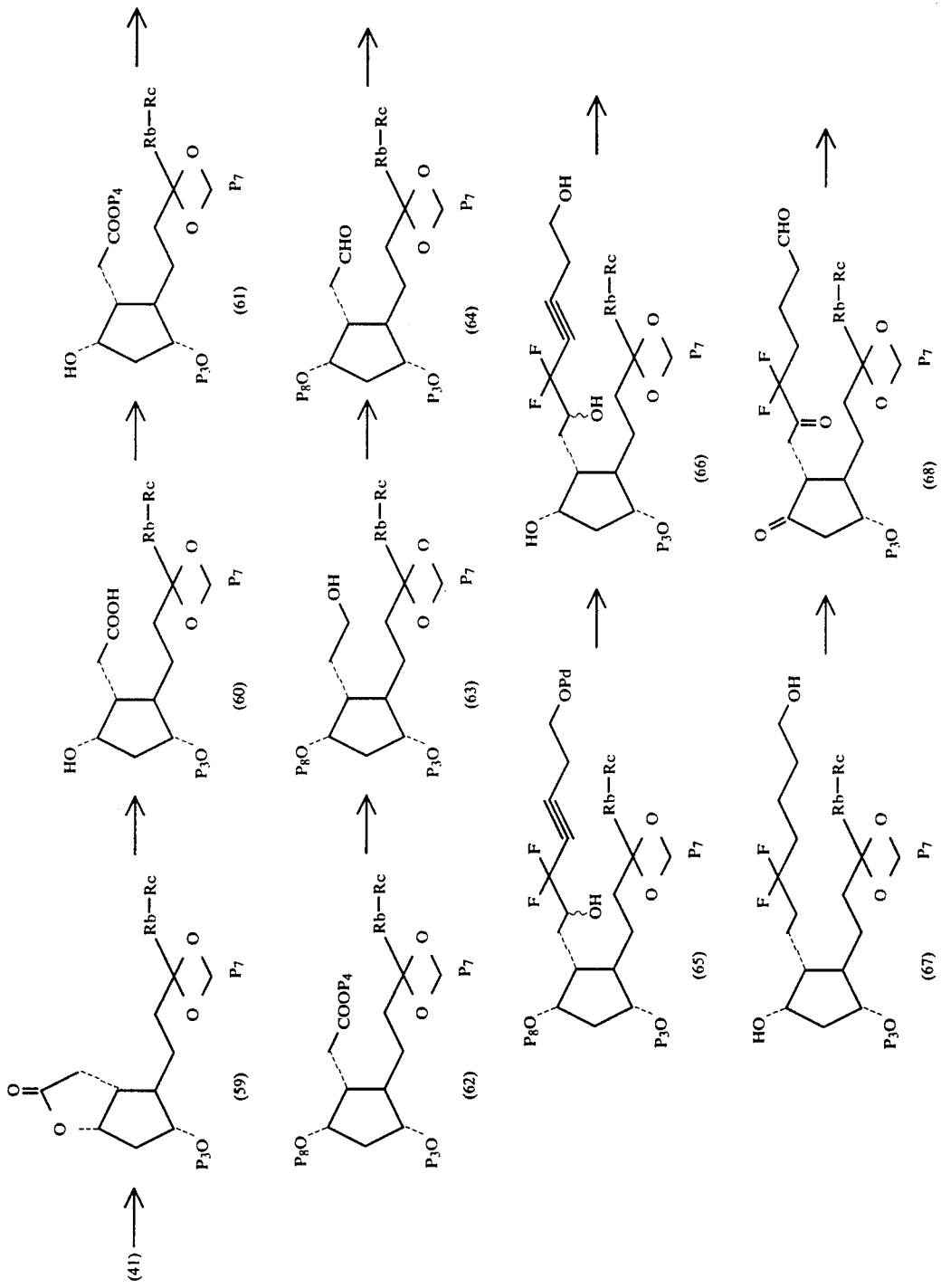

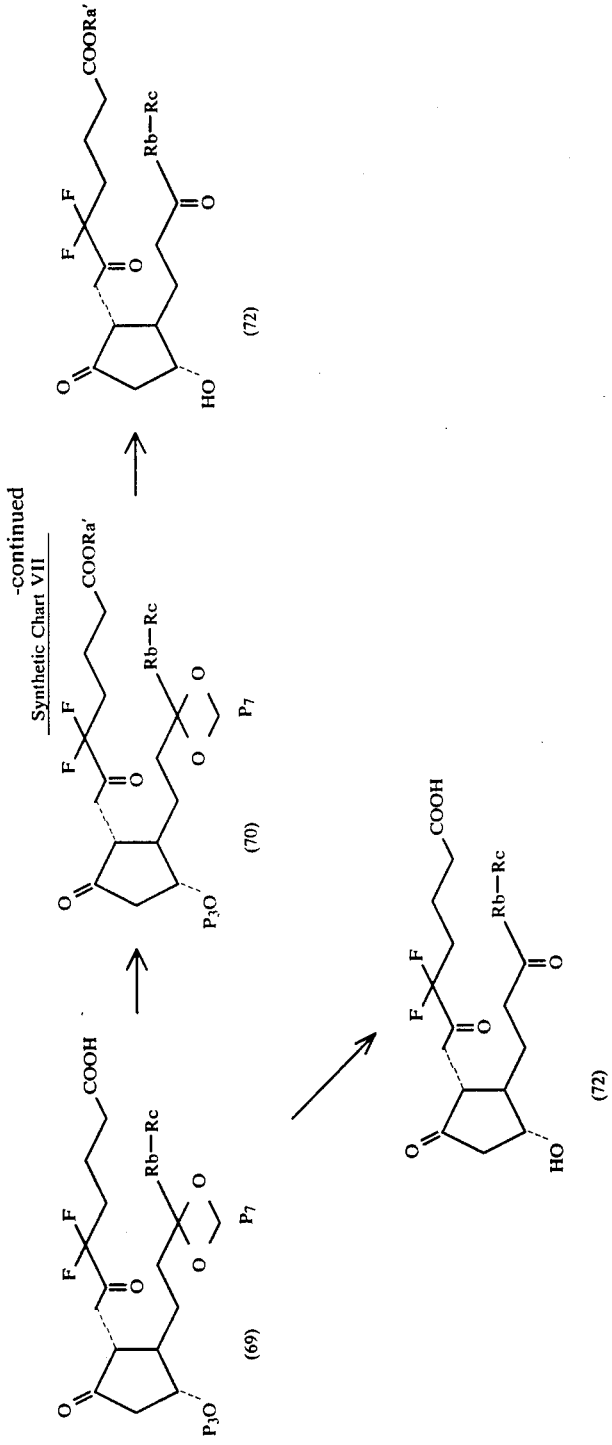

Synthetic Chart VIII

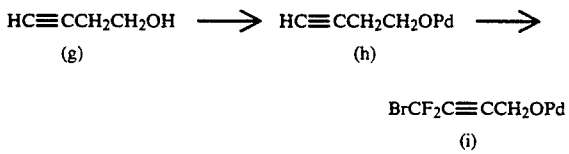

Since the above 15-keto-PG compounds have encephalic metabolism activating action, encephalic function protecting action and encephalic circulation improving action, they are useful in treatment for improving encephalic function. Such activities can be measured by the standard methods, for example, methods using complete ischemic model (for encephalic function protecting action), hypoxia loaded model (for encephalic circulation improving action) etc.

The compounds used in the present invention may be used as a medicine for animals and human beings and usually applied systemically or locally by the method of oral administration, intravenous injection (including instillation), subcutaneous injection, rectal administration and the like. While the dosage will vary depending on the animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As solid composition of this invention for oral administration, tablets, torches, buccals, capsule, pills, powders, granules and the like are included. The solid composition containing one or more active substances is mixed with at least an inactive diluent such as lactose, mannitol, glucose, hydoxypropyl cellulose, micro crystalline cellulose, starch, polyvinyl pyrolidone, magnesium aluminate metasilicate. The composition may contain additives other than the inactive diluent, such as lubricants e.g., magnesium stearate, a disintegrator e.g. cellulose calcium gluconates, stabilizers e.g. $\alpha$, $\beta$- or $\gamma$-cyclodextrins, etherated cyclodextrins (e.g. dimethyl-$\alpha$-, dimethyl-$\beta$-, trimethyl-$\beta$-, or hydroxypropyl-$\beta$-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may form complex to increase the stability of the compounds. The stability may be often increased by forming lyposome with phospholipids. Tablets and pills may be coated with an enteric or gastroenteric film such as white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed such as gelatin. Further, when rapid effect is required, it may be in the form of buccal, in which glycerol, lactose etc are used as a base.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents, suspending agents, sweeteners, flavors, perfumes and preservatives.

The compositions for oral administration may be sprays which contain one or more active substance and can be prepared according to a well known method.

The injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils such as olive oil, alcohols such as ethanol and polysorbates. The composition may contain other additives such as preservatives, wetting agents, emulsifying agents, dispersing agents and the like. These are sterilized by filtration through, e.g. a bacteria-retaining filter, compounding with a sterilizer, gas sterilization or radiation sterilization. These can also be prepared by producing a sterilized solid composition and dissolving in sterilized water or a sterilized solvent for injection before use.

Another formulation according to the present invention is the rectal or vaginal suppository. This can be prepared by mixing at least one active compound according to the invention with a suppository base which may be softened at body temperature, optionally containing non-ion surfactant having appropriate softening temperature for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 16,16-difluoro-13,14-dihydro-15-keto-PGE$_1$ methyl ester (39)

1-1) Preparation of (1S,5R,6R,7R)-6-hydroxymethyl-7-tetrahydropyranyloxy-2-oxabicyclo[3.3.0]octan-3-one (29)

To a solution of commercial Corey lactone (THP-form, 37.9 g) in tetrahydrofuran was added a solution (1.0M, 300 ml) of tetrabutylammonium fluoride in tetrahydrofuran and resulting mixture was stirred at room temperature for 3 hours.

Then the reaction mixture was concentrated under reduced pressure and the residue was subjected to column chromatography to give the title compound (29).

Yield: 21.70 g (82.8%).

1-2) Preparation of (1S,5R,6R,7R)-6-{(E)-4,4-difluoro-5-oxo-2-octenyl}-7-tetrahyiropyranyloxy-2-oxabicyclo-[3.3.0]octan-3-one (31)

A solution (2.0M, 45.5 ml) of oxalyl chloride in methylene chloride was diluted with methylene chloride under an argon atmosphere at $-78°$ C. To this solution was added dropwise dimethylsulfoxide (12.9 ml) and the resulting mixture was stirred for 10 minutes. A solution (1S,5R,6R,7R)-6-hydroxymethyl-7-tetrahydropyranyloxy-2-oxabicylo[3.3.0]octan-3-one (29) (11.65 g) in methylene chloride was added dropwise and the mixture was stirred for 30 minutes. Then triethylamine (56 ml) was added dropwise and stirring was continued for further 1 hour. The reaction mixture was treated in the conventional manner to give the aldehyde (30) as a crude product.

To a solution of thallium ethoxide (3.26 ml) in methylene chloride was added under an argon atmosphere dimethyl 3,3-difluoro-2-oxoheptylphosphonate (11.9 g) and the resulting mixture was stirred for 1 hour. After cooling the solution to 0° C., a solution of the aldehyde (30) obtained above in methylene chloride was added dropwise to said solution and the mixture was stirred at room temperature for 14 hours. The reaction mixture was treated with acetic acid, celite and a saturated aqueous potassium idodide solution and filtered. The filtrate was treated in the conventional manner and the crude product was subjected to column chromatography to give the tile compound (31).

Yield: 7.787 g (44.3%).

1-3) Preparation of (1S,5R,6R,7R)-6-(4,4-difluoro-5-oxooctyl)-7-tetrahydropyranyloxy-2-oxabicyclo[3.3.0]octan-3-one (32)

To a solution of (1S,5R,6R,7R)-6-{(E)-4,4-difluoro-5-oxo-2-octenyl}-7-tetrahydropyranyloxy-2-oxabicyclo[3.3.0]octan-3-one (31) (5.57 g) in ethyl acetate was added 5% Pd/C (catalytic amount) and the resulting mixture was shaken under a hydrogen atmosphere at room temperature for 7 hours. The reaction mixture was filtered and the filtrate was concentrated under reduced pressure to give the tile compound (32) as a crude product. Yield: 5.48 g (97.8%).

1-4) Preparation of (1S,5R,6R,7R)-6-{4,4-difluoro-5(RS)-hydroxyoctyl}-7-tetrahydropyranyloxy-2-oxabicyclo-[3.3.0]-octan-3-one (33)

To a solution of (1S,5R,6R,7R)-6-(4,4-difluoro-5-oxooctyl)-7-tetrahydropyranyloxy-2-oxabicyclo[3.3.0]octan-3-one (32) (5.48 g) in methanol was added sodium borohydride (0.800 g) at 0° C. and the resulting mixture was stirred for 10 minutes. The reaction mixture was treated in the conventional manner and the obtained crude product was subjected to column chromatography to give the title compound (33). Yield: 5.46 g (99.5%).

1-5) Preparation of 16,16-difluoro-13,14-dihydro-11-tetrahydropyranyloxy-PGF$_{2\alpha}$ methyl ester (36)

A solution of (1S,5R,6R,7R)-6-{4,4-dihydro-5(RS)-hydroxyoctyl}-7-tetrahydropyranyloxy-2-oxabicyclo[3.3.0]-octan-3-one (33) (2.579 g) in toluene was cooled to −78° C. under an argon atmosphere. To this solution was added dropwise a solution (1.5M, 9.6 ml) of diisobutylalmium hydride in toluene and stirred for 30 minutes. The reaction mixture was treated with methanol and a saturated aqueous Rochelle salt solution. Then the solution was treated in the conventional manner to give the lactol (34) as a crude product.

To a suspension of 4-carboxybutyl triphenyl phosphine bromide (11.72 g) in tetrahydrofuran was added dropwise under an argon atmosphere a solution (1.0M, 52.84 ml) of potassium tert-butoxide in tetrahydrofuran and the resulting mixture was stirred for 20 minutes. The solution was cooled to 0° C. and combined with a solution of lactol (34) in tetrahydrofuran. The resulting mixture was stirred at room temperature for 15 hours and then treated in the conventional manner to give the carboxylic acid (35) as a crude product.

To a solution of the carboxylic acid (35) in acetonitrile was added under an argon atmosphere 1,8-diazabicyclo[5.4.0]undec-7-ene (DBU) (4.0 ml) and methyl iodide (1.7 ml) and the resulting solution was stirred at 60° C. for 30 hours. The solution was treated in the conventional manner and the product was subjected to column chromatography to give the title compound (36).

Yield: 2.737 g (84.5%).

1-6) Preparation of 16,16-difluoro-13,14-dihydro-15-keto-11-tetrahydropyranyloxy-PGE$_2$ methyl ester (37)

To a solution of Collins reagent, prepared from cromic anhydride (16.18 g) and pyridine (26.2 ml) in the conventional process, in methylene chloride was added a solution of 16,16-difluoro-13,14-dihydro-11-tetrahydropyranyloxy-PGF$_{2\alpha}$ methyl ester (36) (2.646 g) in methylene chloride under an argon atmosphere at −20° C. The resulting mixture was stirred at the same temperature for 2 hours and at −5° C. for 9 hours. The solution was treated with ether and sodium hydrogen sulfate and filtered. The filtrate was concentrated under reduced pressure and the residue was subjected to column chromatography to give the title compound (37). Yield: 1.890 g (64.4%).

1-7) Preparation of 16,16-difluoro-13,14-dihydro-15-keto-PGE$_2$ methyl ester (38)

Into a mixed solvent of acetic acid:water:tetrahydrofuran (3:1:1) was dissolved 16,16-difluoro-13,14-dihydro-15-keto-11-tetrahydroxypyranyloxy-PGE$_2$ methyl ester (37) (2.809 g) and the resulting solution was stirred at 60° C. for 5 hours. The reaction mixture was concentrated under reduced pressure and the residue was subjected to chromatography to give the title compound (38).

Yield: 1.755 g (75.5%).

1-8) Preparation of 16,16-difluoro-13,14-dihydro-15-keto-PGE$_1$ methyl ester (39)

To a solution of 16,16-difluoro-13,14-dihydro-15-keto-PGE$_2$ methyl ester (38) (1.755 g) in ethyl acetate was added Pd/C (catalytic amount) and the mixture was shaken under a hydrogen atmosphere at room temperature for 6 hours. The reaction mixture was filtered. The filtrate was concentrated and the residue was subjected to column chromatography to give the title compound (39).

Yield: 1.655 g (93.8%).

$^1$H NMR(CDCl$_3$) δ0.87(3H,t,J=7 Hz), 1.15–2.05(23H,m), 2.11–2.30(3H,m), 2.50(1H,dd,J=7.5 and 17 Hz), 3.10–3.20 (1H,br), 3.71(3H,s), 4.05–4.20(1H,m)

MS(DI—EI) m/z 404(M+), 355 (M+—H$_2$O—CH$_3$O), 297(M+—C$_5$H$_9$F$_2$)

PREPARATION EXAMPLE 2

Preparation of 16,16-difluoro-13,14-dihydro-15-keto-PGE$_1$ (39')

2-1) Preparation of (15RS)-16,16-difluoro-13,14-dihydro-11-O-tetrahydropyranyl-PGF$_{2\alpha}$ benzyl ester (36)

To a solution of 16,16-difluoro-13,14-dihydro-11-O-tetrahydropyranyl-PGF$_{2\alpha}$ (35) (2.33 g) in dichloromethane (300 ml) were added DBU (2.1 ml) and benzyl bromide (2.2 ml) and the resulting mixture was stirred at room temperature for 1.5 hour. The reaction mixture was treated in the conventional manner and the crude product was purified by silica-gel column chromatography to give the title compound (36). Yield: 2.522 g (96.1%)

2-2) Preparation of 16,16-difluoro-13,14-dihydro-15-keto-11-O-tetrahydropyranyl-PGE$_2$ benzyl ester (37)

Collins reagent was prepared by using chromic anhydride (13.5 g) and pyridine (21.8 ml) in dichloromethane (300 ml), and to this were added Celite (40 g) and (15RS)-16,16-difluoro-13,14-dihydro-11-O-tetrahydropyranyl-PGF$_{2\alpha}$ benzyl ester (36) (2.550 g). The reaction mixture was treated in the conventional manner and the crude product was purified by silica-gel column chromatography to give the title compound (37). Yield: 1.991 g (78.6%)

2-3) Preparation of 16,16-difluoro-13,14-dihydro-15-keto-PGE$_2$ benzyl ester (38)

Into a mixed solvent of acetic acid:THF:water (3:1:1, 50 ml) was dissolved 16,16-difluoro-13,14-dihydro-15-keto-11-O-tetrahydropyranyl-PGE$_2$ benzyl ester (37) (1.550 g) and the solution was kept at 50° C. for 4 hours. The reaction mixture was treated in the conventional manner and the crude product was purified by silica-gel column chromatography to give the title compound (38).

Yield: 1.225 g (92.9%)

2-4) Preparation of 16,16-difluoro-13,14-dihydro-15-keto-PGE$_1$ (39')

To a solution of 16,16-difluoro-13,14-dihydro-15-keto-PGE$_2$ benzyl ester (38) (0.844 g) in ethyl acetate (30 ml) was added 5% Pd/C and the mixture was shaken under a hydrogen atmosphere. The reaction mixture was treated in the conventional manner and the crude product was purified by silica-gel column chromatography to give the title compound (43). Yield: 0.404 g $^1$H NMR(CDCl$_3$) δ0.94 (t,3H,J=7.5 Hz), 1.20–2.70 (m,26H), 4.19 (m,1H), 4.80 (br,2H).

MS(DI—EI) m/z 390(M+), 372(M+—H$_2$O), 354(M+—2H$_2$O)

PREPARATION EXAMPLE 3

Preparation of 5(RS)-fluoro-13,14-dihydro-6,15-diketo-PGE$_1$ methyl ester [IUPAC nomenclature: 5(RS)-fluoro-7-{(1R,2s,3S)-3-hydroxy-2-(3-oxooctyl-5-oxocyclopentyl}-6-oxoheptanoate]

3-1) Preparation of (1S,5R,6R,7R)-6-[(E)-3-oxo-1-octenyl]-7-(4-phenyl)benzoyloxy-2-oxabicyclo[3.3.-0]octan-3-one (42)

Commercial (−)-Corey lactone (40) (10.0 g) in dichloromethane was subjected to Collins oxidation to give the aldehyde (41), which was reacted with an anion prepared from dimethyl (2-oxoheptyl)phosphonate (6.21 g). The reaction mixture was treated in the conventional manner and the obtained crude product was subjected to column chromatography to give the title compound (42).

Yield: 7.45 g (60%)

3-2) Preparation of (1S,5R,6R,7R)-6-[(E)-3(RS)-hydroxy-1-octenyl]-7-(4-phenyl)benzoyloxy-2-oxabicyclo-[3.3.0]-octan-3-one (43)

To a solution of (1S,5R,6R,7R)-6-[(E)-3-oxo-1-octenyl]-7-(4-phenyl)benzoyloxy-2-oxabicyclo-[3.3.0]-octan-3-one (42) (7.45 g) in methanol were added cerium chloride (III) heptahydrate (6.84 g) at −20 ° C. and sodium borohydride (0.69 g) and the mixture was stirred for 1 hour.

The reaction mixture was treated in the conventional manner and the obtained crude product was subjected to the column chromatography to give the title compound (43) as a mixture of the diastereomers.

Yield: 7.64 g (theoretical)

3-3) Preparation of (1S,5R,6R,7R)-6-[(E)-3(RS)-t-butyldimethylsilyloxy-1-octenyl]-7-(4-phenyl)benzoyloxy-2-oxabicyclo[3.3.0]octan-3-one (44)

To a solution of (1S,5R,6R,7R)-6-[(E)-3(RS)-hydroxy-1-octenyl]-7-(4-phenyl)benzoyloxy-2-oxabicyclo-[3.3.0]octan-3-one (43) (7.65 g) in dimethyl formamide were added imidazol (2.27 g) and t-butyldimethylsilyl chloride (3.78 g) and the mixture was stirred for 1 hour.

The reaction mixture was treated in the conventional manner and the obtained crude product was subjected to the silica gel column chromatography to give the title compound (44) as a mixture of the diastereomers.

Yield: 7.49 g (80%)

3-4) Preparation of (1S,5R,6R,7R)-6-[(E)-3(RS)-t-butyldimethylsilyloxy-1-octenyl]-7-hydroxy-2-oxabicyclo-[3.3.0]octan-3-one (45)

A mixture of (1S,5R,6R,7R)-6-[(E)-3(RS)-t-butyldimethylsilyloxy-1-octenyl]-7-(4-phenyl)benzoyloxy-2-oxabicyclo[3.3.0]octane-3-one (44) (7.49 g), potassium carbonate (1.10 g) and methanol was stirred at room temperature for 16 hours. The reaction mixture was treated in the conventional manner and the obtained crude product was subjected to the silica gel column chromatography to give the title compound (45) as a mixture of the diastereomers.

Yield: 4.69 g (92%)

3-5) Preparation of (1S,5R,6R,7R)-6-[(E)-3(RS)-t-butyldimethylsilyloxy-1-octenyl]-7-tetrahydropyranyloxy-2-oxabicyclo[3.3.0]octan-3-one (46)

To a solution of (1S,5R,6R,7R)-6-[(E)-3(RS)-t-butyldimethylsilyloxy-1-octenyl]-7-hydroxy-2-oxabicyclo-[3.3.0]octan-3-one (45) (4.69 g) in methylene chloride were added dihydropyran (5.17 g), and pyridinium p-toluenesufonate (0.77 g), and the resultant mixture was stirred at room temperature for 16 hours. The reaction mixture was treated in the conventional manner and the obtained crude product was subjected to the silica gel column chromatography to give the title compound (46) as a mixture of the diastereomers.

Yield: 5.37 g (94%)

3-6) Preparation of methyl 2-{(1R,2R,3R,5S)-2-[(E)-3(RS)-t-butyldimethylsilyloxy-1-octenyl]-5-hydroxy-tetrahydropyranyloxy-cyclopentyl}acetate (47)

To a solution of (1S,5R,6R,7R)-6-[(E)-3(RS)-t-butyldimethylsilyloxy-1-octenyl]-7-tetrahydropyranyloxy-2-oxabicyclo[3.3.0]octan-3-one (46) (1.85 g) in a mixed solvent of methanol and water (4:1) was added lithium hydroxyde (0.33 g). The resultant mixture was stirred at room temperature for 16 hours. The reaction mixture was neutralized and extracted with ethyl acetate. Then, the organic layer was separated and an ether solution of diazomethane was added thereto. The resultant mixture was stirred at room temperature for 1 hour. The reaction mixture was treated in the conventional manner and the obtained crude product was subjected to the silica gel column chromatography to give the title compound (47) as a mixture of the diastereomers.

Yield: 1.82 g (92%)

3-7) Preparation of methyl 2-{(1R,2R,3R,5S)-2-[(E)-3(RS)-t-butyldimethylsilyloxy-1-octenyl]-3,5-bis-tetrahydropyranyl-oxy-cyclopentyl}acetate (48)

To a solution of methyl 2-{(1R,2R,3R,5S)-2-[(E)-3(RS)-t-butyldimethylsilyloxy-1-octenyl]-5-hydroxytetrahydropyranyloxy-cyclopentyl}acetate (47)(4.45 g) in methylene chloride were added dihydropyran (3.75 g) and pyridinium p-toluenesufonate (0.56 g), and the resultant mixture was stirred at room temperature for 16 hours. The reaction mixture was treated in the conventional manner and the obtained crude product was subjected to the silica gel column chromatography to give the title compound (48) as a mixture of the diastereomers.

Yield: 4.24 g (74%)

3-8) Preparation of methyl 6-benzoyloxy-2(RS)-{2-[(1R,2R,3R,5S)-2-[(E)-3(RS)-t-butyldimethylsilyloxy-1-octenyl]-3,5-bis-tetrahydropyranyloxy-cyclopentyl]-1(RS)-hydroxyethyl}-2(SR)-fluorohexaneacetate (49)

To a toluene solution of methyl 2-{(1R,2R,3R,5S)-2-[(E)-3(RS)-t-butyldimethylsilyloxy-1-octenyl]-3,5-bis-tetrahydropyranyloxy-cyclopentyl}acetate (48) (0.5 g) was added a toluene solution of DIBAL-H (1.5M, 1.43 ml) at −78° C. and the resultant mixture was stirred for 1 hour. The reaction mixture was treated in the conventional manner to give the aldehyde as a crude product.

The solution of LDA, prepared in the conventional manner, in terahydrofuran (0.94 mmol) was cooled to −78° C., and methyl 6-benzoyloxy-2(RS)-fluorohexanoate (f) (0.23 g) was added thereto. The resultant mixture was stirred for 10 minutes and the solution of the crude aldehyde in tetrahydrofran was added thereto. The reaction mixture was heated to room temperature and stirred at the same temperature for 1 hour, The crude product obtained in the conventional manner was subjected to the silica gel column chromatography to give the title compound (49) as a mixture of the diastereomers.

Yield: 0.51 g (74%)

3-9) Preparation of methyl 2(RS)-{2-[(1R,2R,3R,5S)-2-[(E)-3(RS)-t-butyldimethylsilyloxy-1-octenyl]-3,5-bis-tetrahydropyranyloxy-cyclopentyl]-1(RS)-hydroxyethyl}-2(SR)-fluoro-6-hydroxyhexanoate (50)

To a solution of methyl 6-benzoyloxy-2(RS)-{2-[(1R,2R,3R,5S)-2-[(E)-3(RS)-t-butyldimethylsilyloxy-1-octenyl]-3,5-bis-tetrahydropyranyloxy-cyclopentyl]-1(RS)-hydroxyethyl}-2(SR)-fluorohexaneacetate (49) (2.48 g) in methanol was added potassium carbonate (2.47 g) in methanol and the resultant mixture was stirred at room temperature for 24 hours. The crude product obtained in the conventional manner was subjected to the silica gel column chromatography to give the title compound (50).

Yield: 1.50 g (69%)

3-10) Preparation of 7-{(1R,2R,3R,5S)-2-[(E)-3(RS)-t-butyldimethylsilyloxy-1-octenyl]-3,5-bis-tetrahydropyranyloxycyclopentyl]-5(RS)-methoxycarbonyl}-5(SR)-fluoro-6-oxoheptanoate (51)

Methyl 2(RS)-{2-[(1R,2R,3R,5S)-2-[(E)-3(RS)-t-butyldimethylsilyloxy-1-octenyl]-3,5-bis-tetrahydropyranyloxycyclopentyl]-1(RS)-hydroxyethyl}-2(SR)-fluoro-6-hydroxyhexanoate (50) (1.23 g) was subjected to Collins oxidation at −50° C. under an argon atmosphere for 4.5 hours. The crude product obtained in the conventional manner was dissolved into ether, and a solution of diazomethane in ether was added thereto. The resultant mixture is stirred at room temperature for 1 hour. The reaction mixture was treated in the conventional manner and the obtained crude product was subjected to the silica gel column chromatography to give the title compound (51) in the form of diastereomeric mixture. Unreacted starting material (50) was recovered (0.41 g, Recovery: 33%).

Yield: 0.60 g (47%)

3-11) Preparation of methyl 7-{(1R,2R,3R,5S)-2-[(E)-3(RS)-t-butyldimethylsilyloxy-1-octenyl]-3,5-bis-tetrahydropyranyloxycyclopentyl]-5(RS)-fluoro-6-oxo-heptanoate (52)

Methyl 7-{(1R,2R,3R,5S)-2-[(E)-3(RS)-t-butyldimethylsilyloxy-1-octenyl]-3,5-bis-tetrahydropyranyloxy-cyclopentyl]-5(RS)-methoxycarbonyl-5(SR)-fluoro-6-oxoheptanoate (51) (0.80 g) was dissolved into a mixture of dimethyl sulfoxide, sodium chloride and water (50:2.8:1) and the resultant mixture was stirred at 135°–140° C. under an argon atmosphere for 1.5 hours. The crude product obtained by treating in the conventional manner was subjected to silica gel column chromatography to give the title compound (12) as a mixture of diastereomers.

Yield: 0.55 g (75%)

3-12) Preparation of methyl 5(RS)-fluoro-7-{(1R,2R,3R,5S)-2-[(E)-3(RS)-t-hydroxy-1-octenyl]-3,5-bis-tetrahydropyranyloxycyclopentyl]-6-oxoheptanoate (53)

To a solution of methyl 7-{(1R,2R,3R,5S)-2-[(E)-3(RS)-t-butyldimethylsilyloxy-1-octenyl]-3,5-bis-tetrahydropyranyloxy-cyclopentyl]-5(RS)-fluoro-6-oxoeptanoate (52) (0.52 g) in tetrahydrofuran was added a solution of tetra-n-butylammonium fluoride in tetrahydrofuran (1M, 23 ml), and the resultant mixture was stirred at room temperature for 40 hours. The crude product obtained by treating in the conventional manner was subjected to silica gel chromatography to give the title compound (53).

Yield: 0.34 g (67%)

3-13) Preparation of methyl 5(RS)-fluoro-7-{(1R,2R,3R,5S)-2-[3(RS)-hydroxy-1-octyl]-3,5-bis-tetrahydropyranyloxycyclopentyl]-6-oxoheptanoate (54)

To a solution of methyl 5(RS)-fluoro-7-{(1R,2R,3R,5S)-2-[(E)-3(RS)-t-hydroxy-1-octenyl]-3,5-bis-tetrahydropyranyloxycyclopentyl]-6-oxoheptanoate (53) in ethyl acetate was added 5% of Pd/C (0.06 g), and the resultant mixture was stirred at room temperature under a hydrogen atmosphere for 16 hours. The reaction mixture was treated in the conventional manner and the obtained crude product was subjected to silica gel column chromatography to give the title compound (54) as a mixture of diastereomers.

Yield: 0.30 g (88%)

3-14) Preparation of methyl 5(RS)-fluoro-7-{(1R,2R,3R,5S)-2-[3-oxo-octyl]-3,5-bistetrahydropyranyloxy-cyclopentyl]-6-oxoheptanoate (55)

To a solution of methyl 5(RS)-fluoro-6-oxo-7-{(1R,2R,3R,5S)-2-[3(RS)-hydroxy-1-octyl]-3,5-bis-tetrahydropyranyloxy-cyclopentyl]-6-oxo-heptanoate (54) (0.30 g) in acetone was added Jones reagent (2.60M, 0.6 ml) and the resultant mixture was stirred at −30° C. for 1.5 hours. The reaction mixture was treated in the conventional manner and the obtained crude product was subjected to silica gel column chromatography to give the title compound (55) as a mixture of diastereomers.

Yield: 0.24 g (80%)

3-15) Preparation of methyl 5(RS)-fluoro-7-{(1R,2R,3R)-3-t-butyldimethylsilyloxy-5-oxo-2-(3-oxo-octyl)-cyclopentyl]-6-oxoheptanoate (57)

Methyl 5(RS)-fluoro-6-oxo-7-{(1R,2R,3R,5S)-2-[3-oxo-octyl]-3,5-bis-tetra-hydropyranyloxy-cyclopentyl]-6-oxo-heptanoate (55) (0.24 g) was dissolved into a mixed solvent of acetic acid, tetrahydrofuran and water (3:1:1), and the resultant mixture was stirred at 45° C. for 4.5 hours. The crude product obtained by treating in the conventional manner was subjected to silica gel column chromatography to give a diol product (56) (0.15 g).

To a solution of diol product (56) (0.15 g) in dimethylformamide were added imidazol (0.35 g) and t-butyldimethylsilyl chloride (0.38 g) and the resultant mixture was stirred at room temperature for 5 hours. The crude product obtained by treating in the conventional manner was subjected to silica gel column chromatography to give monosilyl product (0.135 g).

The monosilyl product (0.135 g) was subjected to Collins oxidation in methylene chloride at room temperature for 15 minutes. The crude product obtained by treating in the conventional manner was subjected to silica gel column chromatography to give the title compound (57).

Yield: 0.10 g (49%, starting from Compound (55))

3-16) Preparation of 5(RS)-fluoro-13,14,-dihydro-6,15-diketo-PGE$_1$ methyl ester (58)

To a solution of methyl 5(RS)-fluoro-7-{(1R,2R,3R)-3-t-butyldimethylsilyloxy-5-oxo-2-(3-oxooctyl)-cyclopentyl]-6-oxoheptanoate (57) (0.05 g) in dichloromethane was added a solution of hydrogen fluoride-pyridine (70:30, 0.40ml), and the resultant mixture was stirred at room temperature for 7 hours. The crude product obtained by treating in the conventional manner was subjected to silica gel column chromatography to give the title compound (58).

Yield: 0.38 g (98%)

$^1$H NMR (CDCl$_3$) δ 0.87(3H,t,J=6.8 Hz), 1.16–2.05(14H,m), 2.23–3.15(11H,m), 3.66(3H,s), 3.98–4.12(1H,m), 4.62–4.70(0.5H,m), 4.85–4.95(0.5H,m).

Preparation of Starting Material: Methyl 6-benzoyloxy-2(RS)-fluoro-hexanoate (f)

1) Preparation of benzyl 6-hydroxyhexanoate (b)

A mixture of ε-caprolactone (a) (40 g), benzyl alcohol and p-toluenesulfonic acid monohydrate (0.7 g) was stirred at 100° C. for 16 hours. The reaction mixture was treated in the conventional manner and was distilled under reduced pressure (1 mmHg, 140°–154° C.) to give the title compound (b).

Yield: 27.37 g (35%)

2) Preparation of benzyl 6-benzoyloxyhexanoate (c)

To a solution of benzyl 6-hydroxyhexanoate (b) (27.37 g) in methylene chloride were added 4-dimethyl amino pyridine (19.5 g) and benzoyl chloride (19.53 g), and the resultant mixture was stirred for 2 hours. The reaction mixture was treated in the conventional manner and was distilled under reduced pressure (1 mmHg, 190°–215° C.) to give the title compound (c).

Yield: 38.09 g (95%)

3) Preparation of 6-benzoyloxy-hexanoic acid (d)

To a solution of benzyl 6-benzoyloxy-hexanoate (c) (38.09 g) in ethyl acetate was added 5% Pd/C (3 g) and the resultant mixture was stirred under a hydrogen atmosphere for 24 hours. The crude product obtained by treating in the conventional manner was distilled under reduced pressure (1 mmHg, 182°–192° C.) to give the title compound (d).

Yield: 4.92 g (90%)

4) Preparation of methyl 6-benzoyloxy-2(RS)-bromohexanoate (e)

Thionyl chloride (22 ml) was added dropwise to 6-benzoyloxyhexanoic acid (d) (14.92 g), and the resultant mixture was stirred at 65° C. for 1 hour. To the reaction mixture were added carbon tetrachloride (50ml), N-bromosuccinimide (22.5 g) and 48% hydrobromic acid (5 drops), and the resultant mixture was stirred at 85° C. for 20 hours. The reaction mixture was allowed to cool, and was filtered to remove solid product. The filtrate was concentrated under reduced pressure. The obtained residue was dissolved into methanol and the resultant mixture was stirred at room temperature. The crude product obtained by treating in the conventional manner was subjected to silica gel chromatography to give the title compound (e).

Yield: 14.02 g (67%)

5) Preparation of methyl 6-benzoyloxy-2(RS)-fluorohexanoate (f)

A mixture of methyl 6-benzoyloxy-2(RS)-bromohexanoate (e) (14.02 g), potassium fluoride (12.59 g) and acetamide (12.3 g) was stirred at 105° C. for 6 hours. The crude product obtained by treating in the conventional manner was subjected to silica gel chromatography to give the title compound (f) and methyl 6-benzoyloxyhexanoate (g) (3.11 g, yield: 29%).

Yield: 5.28 g (46%)

$^1$H NMR (CDCl$_3$)δ: 1.55–2.18 (6H,m), 3.79(3H,s), 4.33(2H,t,J=7 Hz), 4.77–4.86(0.5H,m), 5.05–5.12(0.5H,m), 7.40–7.62(3H,m), 8.00–8.10(2H,m).

PREPARATION EXAMPLE 4

Preparation of 5,5-difluoro-13,14-dihydro-6,15-diketo-PGE$_1$ methyl ester (72)

4-1) Preparation of (1S,5R,6R,7R)-6-[(E)-3-oxo-1-octenyl]-7-(4-phenylbenzoyloxy)-2-oxabicyclo[3.3.0]-octan-3-one (42)

Corey-lactone (40) (10.0 g) dissolved in dichloromethane (160ml) was subjected to Moffatt oxidation using DMSO (79.2 g), dicyclohexylcarbodiimide (24.0 g), pyridine (2.3 ml) and trifluoroacetic acid (1.1 ml) to give Corey-lactone aldehyde (2a). Separately, dimethyl (2-oxoheptyl)phosphonate anion was prepared from dimethyl-(2-oxoheptyl)phosphonate (6.31 g) and sodium hydride (60%, 0.13 g) in dichloromethane, and the solution of the previously obtained aldehyde (160 ml) was added dropwise thereto, and the resultant mixture was stirred at room temperature for 11.5 hours. The crude product obtained by treating in the conventional manner was subjected to silica gel chromatography to give the title compound (42).

Yield: 10.8 g (85.3%)

4-2) Preparation of (1S,5R,6R,7R)-6-(3-oxo-1-octenyl)-7-(4-phenylbenzoyloxy)-2-oxabicyclo[3.3.0]octan-3-one (4a)

A mixture of (1S,5R,6R,7R)-6-[(E)-3-oxo-1-octenyl]-7-(4-phenylbenzoyloxy)-2-oxabicycloctan[3.3.0]-3-one (42) (10.8 g) and 5% Pd/C (1.02 g) in ethyl acetate (150 ml) was stirred under a hydrogen atmosphere for 3 hours. The reaction mixture was treated in the conventional manner to give the title compound (4a).

Yield: 8.20 g 4-3) Preparation of (1S,5R,6R,7R)-6-(3,3-ethylenedioxyoctyl-7-(4-phenylbenzoyloxy)-2-oxabicyclo[3.3.0]-octan-3-one (5)

To a solution of (1S,5R,6R,7R)-6-(3-oxo-1-octenyl)-7-(4-phenylbenzoyloxy)-2-oxabicyclo[3.3.0]octan-3-one (4a) (8.20 g) in toluene (100 ml) were added ethylene glycol (23.0 g) and p-toluenesulfonic acid (0.41 g), and the resultant mixture was refluxed for 4 hours. Water formed in the reaction was removed by azeotropic distillation. The reaction mixture was treated in the conventional manner and was subjected to silica gel column chromatography to give the title compound (5a).

Yield: 8.23 g (91.3%)

4-4) Preparation of (1S,5R,6R,7R)-6-(3,3-ethylenedioxyoctyl)- 7-hydroxy-2-oxabicyclo[3.3.0]octan-3-one (6a)

To a solution of (1S,5R,6R,7R)-6-(3,3-ethylenedioxyoctyl-7-(4-phenylbenzoyloxy)-2-oxabicyclo[3.3.0]octan-3-one (5a) (8.20 g) in methanol (200 ml) was added potassium carbonate (1.15 g) and the resultant mixture was stirred overnight, and acetic acid (1 ml) was added thereto. The crude product obtained by treating in the conventional manner was subjected to silica gel column chromatography to give the title compound (6a).

Yield: 4.70 g (90.0%)

4-5) Preparation of (1S,5R,6R,7R)-6-(3,3-ethylenedioxy-octyl)-7-tetrahydropyranyloxy-2-oxabicyclo[3.3.0]octan-3-one (59)

A solution of (1S,5R,6R,7R)-6-(3,3-ethylenedioxyoctyl)-7-hydroxy-2-oxabicyclo[3.3.0]octan-3-one (6a) (4.70 g) in dichloromethane (200 ml) was cooled on ice and dihydropyran (2.41 g) and p-toluenesulfonic acid (0.23 g) were added thereto and the resultant mixture was stirred for 1,5 hours. The crude product obtained by treating in the conventional manner was subjected to silica gel column chromatography to give the title compound (59).

Yield: 5.54 g (93%)

4-6) Preparation of methyl 2-[(1S,2R,3R,5S)-2-(3,3-ethylenedioxy-octyl)-3-(tetrahydropyranyloxy)- 5-hydroxycyclopentyl]acetate (61)

(1S,5R,6R,7R)-6-(3,3-ethylenedioxyoctyl)-7-tetrahydropyranyloxy-2-oxabicyclo[3.3.0]octan-3-one (59) (5.54 g) was dissolved into methanol (61 ml), and 5% aqueous potassium hydroxyde (37 ml) was added thereto. The resultant mixture was stirred at 50° C. for 30 minutes. While cooling on ice, the reaction mixture was neutralized with aqueous 0.5N hydrochloric acid and the acid (60) obtained by treating in the conventional manner was treated with diazomethane to give the title compound (61).

Yield: 5.74 g 4-7) Preparation of methyl 2-[(1S,2R,3R,5S)-2-(3,3-ethylenedioxyoctyl)-3-(tetrahydropyranyloxy)-5-(t-butylsilyloxy)cyclopentyl]acetate (62)

To a solution of methyl 2-[(1S,2R,3R,5S)-2-(3,3-ethylenedioxyoctyl)-3-(tetrahydropyranyloxy)-5-hydroxycyclopentyl]acetate (61) in DMF (80 ml) were added t-butyldimethylsilyl chloride (2.11 g) and imidazol (0.95 g), and the resultant mixture was stirred. The crude product obtained by treating in the conventional manner was subjected to silica gel column chromatography to give the title compound (62).

Yield: 5.41 g (71.2 g)

4-8) Preparation of 2-[(1S,2R,3R,5S)-2-(3,3-ethylenedioxy-octyl)-3-(tetrahydropyranyloxy)-5 (t-butyldimethylsilyloxy)cyclopentyl]ethanol (63)

Methyl 2-[(1S,5R,6R,7R)-2-(3,3-ethylenedioxyoctyl)-3-(tetrahydropyranyloxy)-5-(t-butyldimethylsiloxy)-cyclopentyl]acetate (62) was reduced with lithium aluminium hydride in ether (150 ml). The crude product obtained by treating in the conventional manner was subjected to silica gel column chromatography to give the title compound (63).

Yield: 4.81 g (93.8%)

4-9) Preparation of 2-[(1S,5R,6R,7R)-2-(3,3-ethylene-dioxy-octyl)-3-(tetrahydropyranyloxy)-5-(t-butyl-dimethylsilyloxy)cyclopentyl]acetaldehyde (64)

A solution of 2-[(1S,5R,6R,7R)-2-(3,3-ethylenedioxy-octyl)-3-(tetrahydropyranyloxy)-5-(t-butylsiloxy) cyclopentyl]ethanol (63) in dichloromethane (50 ml) was subjected to Swan oxidation using oxalyl chloride (1.78 g), DMSO (2.19 g) and triethylamine (4.37 g) to give the title compound (12).

Yield: 4.60 g (96.0%)

4-10) Preparation of 1-[(1R,2R,4S,5R)-2-tetrahydropyranyloxy-4-t-butylsilyloxy-5-(2(RS)-hydroxy-3,3-difluoro-7-t-butyldimethylsilyloxy-4-heptynyl}-cyclopentyl]-3,3-ethylenedioxy-octane (65)

To a solution of 2-[(1S,2R,3R,5S)-2-(3,3-ethylenedioxyoctyl)-3-(tetrahydropyranyloxy)-5-(t-butylsiloxy)-cyclopentyl]acetaldehyde (64) (1.00 g) in THF (25 ml) was added activated zinc powder (2.54 g), and while cooling on ice, the solution of 1-bromo-1,1-difluoro-5-(t-butyl-dimethylsilyloxy)-2-pentyne (i) (0.92 g) in THF (5 ml) was added dropwise the resultant mixture. To the resultant solution was added mercury chloride (0.11 g) and the resultant mixture was stirred under ultrasonic irradiation. The reaction mixture was treated in the conventional manner and the obtained crude product was subjected to silica gel column chromatography to give the title compound (65).

Yield: 1.40 g (95.9%)

4-11) Preparation of 1-{(1R,2R,4S,5R)-2-tetrahydropyranyloxy-4-hydroxy-5-(2(RS),7-dihydroxy-3,3-difluoro-4-heptyl}cyclopentyl]-3,3-ethylenedioxyoctane (67)

A solution of 1-[(1R,2R,4S,5R)-2-tetrahydropyranyloxy-4-t-butylsilyloxy-5-{2(RS)-hydroxy-3,3-difluoro-7-t-butyldimethylsilyloxy-4-heptynyl}cyclopentyl]-3,3-ethylenedioxy-octane (65) (0.96 g) in THF (15 ml) was cooled on ice and tetrabutyl ammonium fluoride (1M, 0.57 ml) was added thereto and the resultant mixture was stirred for 12 hours. The reaction mixture was treated in the conventional manner and the obtained crude product was subjected to silica gel chromatography to give the triol (66) (0.492 g).

The triol (66) was subjected to catalytic hydrogenation over 5% Pd/C (0.06 g) in ethyl acetate (50 ml). The reaction mixture was treated in the conventional manner and the obtained crude product was subjected to silica gel chromatography to give the title compound (67).

Yield: 0.487 g (98.6%)

4-12) Preparation of 5,5-difluoro-6-keto-11-pyranyloxy-15,15-ethylenedioxy-13,14-dihydro-PGE$_1$ methyl ester (70)

A solution of 1-[(1R,2R,4S,5R)-2-tetrahydropyranyloxy-4-hydroxy-5-{2(RS),7-dihydroxy-3,3-difluoro-4-heptynyl}cyclopentyl]-3,3-ethylenedioxyoctane (67) (0.487 g) in dichloromethane (18 ml) was subjected to Swan oxidation using oxalyl chloride (1.17 g), DMSO (1.51 g) and triethylamine (3.1 g) to give the diketoaldehyde (68) (0.321 g, Y: 67.3%).

The obtained diketoaldehyde (68) (0.212 g) was subjected to Jones oxidation using Jones reagent (2.67M 153.6μ) at a temperature between −50° C. and −40° C. to give the carboxylic acid (69), which was reacted with diazomethane in order to obtain methyl ester. The obtained crude product was subjected to silica gel column chromatography to give the title compound (70).

Yield: 0.152 g (67.8%)

4-13) Preparation of 5,5-difluoro-13,14-diketo-PGE$_1$ methyl ester (72)

A solution of 5,5-difluoro-6-keto-11-pyranyloxy-13,14-dihydro-15,15-ethylenedioxy-PGE$_1$ methyl ester (70) (0.152 g) in a mixed solvent of acetic acid/THF/water (2/1/1) (6 ml) was kept at 45°–50° for 2.5 hours. The reaction mixture was treated in conventional manner and the obtained crude product was subjected to silica gel column chromatography to give the title compound (72).

Yield: 0.101 g (87.0%)

\* 13,14-dihydro-6,15-diketo-5,5-difluoro-PGE$_1$ methyl ester $^1$H NMR (CDCl$_3$) δ0.88(t,3H,J=6.6 Hz), 1.10–1.40(m,4H), 1.45–2.20(m,10H), 2.20–3.15(m,11H), 3.67(s,3H), 4.00–4.18 (m,1H)

MS(DI/EI) m/z 418(M$^+$), 400(M$^+$—H$_2$O), 360(M$^+$—HF—H$_2$O), 99(C$_6$H$_{11}$CO$^+$)

Preparation of Starting Material:5-(t-butyldimethylsiloxy)-1-bromo-1,1-difluoro-3-pentyne (i)

1) Preparation of 5-(t-butyldimethylsiloxy)-3-pentyne (h)

To a solution of 3-butyn-1-ol (g) (10.0 g) in DMF (80 ml) were added t-butyldimethylsilyl chloride (21.5 g) and imidazol (10.6 g), and the resultant mixture was kept at 35° C. for 7 hours. The reaction mixture was treated in the conventional manner and the obtained crude product was distilled to give the title compound (h).

Yield: 17.4 g (66%)

2) Preparation of 5-(t-butyl-dimethylsiloxy-1-bromo-1,1-difluoro-3-pentyne) (i)

A solution of 5-(t-butyldimethylsiloxy)-3-pentyne (h) (8.00 g) in THF (100 ml) was cooled to −20° C. and n-butyl lithium (1.6M, 27.1 ml) was added dropwise thereto. The resultant mixture was stood at 0° C. and a solution of dibromodifluoromethane in THF (5 ml) was added, and the mixture was stirred for 2 hours. The reaction mixture was treated in the conventional manner and the obtained crude product was subjected to silica gel column chromatography to give the title compound (i).

Yield: 3.67 g (27%)

| Formulation Example 1 (powders for injection) | |
|---|---|
| | (Parts by weight) |
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

| Formulation Example 2 (Injectable solution) | |
|---|---|
| | (Parts by weight) |
| 13,14-dihydro-15-keto-6,16-difluoro-PGE$_1$ methyl ester | 0.2 |
| nonionic surfactant | 2 |
| sterilized water for injection | 98 |

The above ingredients were mixed and sterilized to give an injectable solution.

FORMULATION EXAMPLE 3

Into methanol (10 ml) was dissolved 13,14-dihydro-15-keto-16,16-difluoro-20-methyl-PGE$_2$ (50 mg) and the produces solution was mixed with mannitol (18.5 g). The mixture was passed through a sieve (pore size: 30 mm), dried at 30° C. for 90 minutes and then sieved again. The produces powders were mixed with microfine silica (Aerosil, 200 g) and the mixture was filed into No.3 hard gelatine capsule shells (100). The capsules were enteric capsules containing 0.5 mg 13,14-dihydro-15-keto-16,16-difluoro-20-methyl-PGE$_2$ per a capsule.

| Formulation Example 4 (Powders for oral administration) | |
|---|---|
| | (Parts by weight) |
| 13,14-dihydro-6,15-diketo-16,16-difluoro-PGE$_1$ methyl ester | 5 |
| light anhydrous silicic acid | 5 |
| Abicel | 20 |
| lactose | 70 |

The above ingredients were mixed to give powders for oral administration.

| Formulation Example 5 (Soft gelatine capsules) | |
|---|---|
| | (Parts by weight) |
| 13,14-dihydro-6,15-diketo-5,5-difluoro-PGE$_1$ methyl ester | 1 |
| light anhydrous silicic acid | 899 |
| Panasate | 20 |

The above ingredients were mixed and filled in soft gelatine capsules.

In the above formulation examples, the active ingredient can be replaced by any other compound within the compounds used in the invention.

Biological Tests

Test Example 1

As the test animals, 10–12/group male Slc-ddY mice (5 weeks old, 27–30 g) were used.

For subcutaneous or intravenous administration, test compounds were dissolved in Ringer solution in such amount that the obtained solution can be administered at 10 ml/kg body weight.

The mice were divided according to their weight into groups with even mean weight, each group consisting of 12 animals.

(a) The mice were decaptated by guillotine at 30 minutes after the administration and cephala were placed in stainless steel vats. Duration of gasping, i.e. panting movement with mouth open and close, expressed after the decapitation, was measured by stopwatch.

(b) The mice revceived 4 mg/kg KCN intravenously and survival time was measured based on heartbeat as an index.

The results are shown in the following Table.

(a) Duration of Gasping

| | Dose (mg/kg, s.c.) | Number of Animals | Duration of Gasping (sec.) Mean ± S.D. |
|---|---|---|---|
| Control | 0 | 11 | 22.4 ± 1.2 |
| Compound 1 | 1.0 | 12 | \*\*24.9 ± 2.2 |
| | 0.3 | 12 | \*24.2 ± 1.9 |
| | 0.1 | 10 | 22.7 ± 1.7 |
| Compound 2 | 0.1 | 11 | \*\*25.0 ± 1.7 |
| | 0.03 | 10 | \*26.1 ± 2.6 |
| | 0.01 | 10 | 23.8 ± 2.5 |
| | 0.003 | 10 | \*24.1 ± 1.7 |
| | 0.001 | 12 | 22.5 ± 1.8 | t-test: \*\*P < 0.01 \*0.05 < P < 0.01 v.s. Control
Compound 1: 13,14-dihydro-15-keto-16R,S-fluoro-PGE$_2$
Compound 2: 13,14-dihydro-15-keto-16,16-difluoro-PGE$_2$ In another run, when 13,14-dihydro-15-keto-16R,S-fluoro-PGE$_2$ methyl ester, 13,14-dihydro-15-keto-16R,S-fluoro-PGE$_2$ ethyl ester and 13,14-dihydro-15- keto-16,16-fluoro-PGE$_2$ methyl ester, as the test compounds, were subcutaneously administered, elongation induration of gasping was observed at doses of 5 mg/kg, 1 mg/kg and 0.3 mg/kg, respectively.

In a further run, when 13,14-dihydro-15-keto-16R,S-fluoro-PGE$_2$, 13,14-dihydro-15-keto-16R,S-fluoro-PGE$_2$ methyl ester and 13,14-dihydro-6,15-diketo-19-methyl-PGE$_1$ ethyl ester, as the test compounds, were intravenously administered, elongation in duration of gasping was observed at doses of 1 mg/kg, 3 mg/kg and 10 mg/kg, respectively.

(b) Survival Time

|  | Dose (mg/kg, s.c.) | Number of Animals | Survival Time (min.-sec.) Mean ± S.D. |
|---|---|---|---|
| Control | 0 | 12 | 9-32 ± 1-48 |
| Compound 1 | 0.3 | 10 | **16-42 ± 3-36 |
|  | 0.1 | 10 | **13-09 ± 2-10 |
|  | 0.03 | 10 | 8-45 ± 1-16 | t-test: **P < 0.01

Compound 1: The same as in (a)

The above results indicate that the duration of gasping and the survival time were elongated by administration of 15-keto-PG compounds.

Test Example 2

Male Crj-Wistar rats (weight: 250-350 g) were anesthetized by intraperitoneal administration of urethane (1.2 g/kg). Test compounds in solutions were administered at a dose of 0.5 ml/kg through a cannula inserted into the femoral vein. Tissue blood stream (ml/100 g/min.) in hippocampus of brain was measured by the hydrogen clearance method, using a tissue rheometer, at 10 minutes before, directly after, 10 minutes after and 20 minutes after (and further 40 minutes after) the administration. The results are shown in the following Table.

|  | Time (min.) | | | | |
|---|---|---|---|---|---|
|  | −10 | 0 | 10 | 20 | 40 |
| Compound 2 | | | | | |
| 0.1 mg/kg | 62.1 | 67.9 | 67.9 | 67.9 | 62.1 |
|  | (100) | (109) | (109) | (109) | (100) |
| 1.0 mg/kg | 41.5 | 58.2 | 62.1 | 62.1 | 48.4 |
|  | (100) | (140) | (150) | (150) | (117) |
| Compound 3 | | | | | |
| 11 mg/kg | 58.0 | 63.5 | 63.5 | 62.1 | |
|  | (100) | (109) | (109) | (107) | |
| DMCD | | | | | |
| 10 mg/kg | 59.5 | 62.1 | 55.8 | 57.0 | |
|  | (100) | (104) | (94) | (96) | |

(Values in parenthese indicate percentage taking the corresponding values at 10 minutes before the administration as 100. DMCD (α-dimethylcyclodextrin) was used as reference because the Compound 3 used in the test was in DMCD adduct form.)
Compound 2: The same as in Test Example 1(a)
Compound 3: 13,14-dihydro-6,15-diketo-19-methyl-PGE$_1$ ethyl ester DMCD adduct (1:10)

The above results indicate that the blood stream in hippocampus was increased by administration of Compound 2 and Compound 3. In addition, results obtained by administering 1.0 mg/kg of Compound 2 indicate that the effect of the compound was more pronounced in the animal having reduced blood stream in hippocampus (assumably by anesthesia and loss of blood on operation).

Test Example 3

Dogs (weight: 8-10 kg) were sacrificed by bleeding under anesthesia with Ketamine and the middle cerebral artery was removed. A ring sample of about 4 mm prepared from said artery was hung in a Magnus tube, containing a nutrient solution, by means of two L-shaped rods. The sample was stretched by 1 g of tension and change in tension was recorded isometrically on a recorder through a transducer. After resting for about 90 minutes, the sample was contracted with $3 \times 10^{-7}$M serotonin (5-HT) and when the contraction reached the peak, test compound was accumulately added. Rate of inhibition of the contraction by the test compounds were expressed in percent taking the contraction $3 \times 10^{-7}$M serotonin as 100.

The result are shown in the following Table.

|  | Concentration | | |
|---|---|---|---|
|  | $10^{-8}$M | $10^{-7}$M | $10^{-6}$M |
| Compound 2 | 11.3% | 18.8% | |
| Compound 3 | 5.1% | 13.1% | 20.1% |
| DMCD | −0.8% | 2.8% | 1.5% |

DMCD was used as reference because the compound 3 used in the test was in DMCD adduct form.

The above results indicate that cerebrovascular contraction was inhibited (i.e. the artery was relaxed) by administration of Compound 2 and Compound 3.

Test Example 4

The procedure of Test Example 1(a) was repeated using other compounds than Compound 1 and Compound 2.

The results are shown in the following Table.

|  | Dose (mg/kg, s.c.) | Duration of Gasping (sec.) Mean ± S.D. |
|---|---|---|
| Control | 0 | 21.6 ± 1.2 |
| Compound 4 | 0.3 | **25.8 ± 1.6 |
|  | 0.1 | *22.8 ± 1.7 |
| Control | 0 | 21.3 ± 1.2 |
| Compound 5 | 0.1 | **23.9 ± 1.4 |
|  | 0.03 | 22.0 ± 1.7 |
| Control | 0 | 22.7 ± 1.3 |
| Compound 6 | 0.1 | *24.0 ± 1.4 |
|  | 0.03 | 23.3 ± 3.1 |
| Control | 0 | 22.7 ± 1.3 |
| Compound 7 | 0.3 | **24.9 ± 1.6 |
|  | 0.1 | 23.6 ± 2.0 |
| Control | 0 | 22.1 ± 1.8 |
| Compound 8 | 1 | **24.2 ± 1.4 |
|  | 0.3 | 23.5 ± 2.1 |
| Control | 0 | 22.7 ± 1.3 |
| Compound 9 | 1 | **24.8 ± 2.7 |
|  | 0.3 | 23.6 ± 1.6 |
| Control | 0 | 22.6 ± 1.6 |
| Compound 10 | 3 | *24.1 ± 1.8 |
|  | 1 | 23.6 ± 1.6 |
| Control | 0 | 22.0 ± 1.8 |
| Compound 11 | 1 | **26.0 ± 2.4 |
|  | 0.3 | 22.6 ± 2.0 |
| Control | 0 | 22.0 ± 2.0 |
| Compound 12 | 0.3 | **25.1 ± 1.9 |
|  | 0.1 | 23.5 ± 2.1 |

-continued

| | Dose (mg/kg, s.c.) | Duration of Gasping (sec.) Mean ± S.D. |
|---|---|---|
| Control | 0 | 21.0 ± 1.9 |
| Compound 13 | 0.3 | **23.9 ± 1.8 |
| | 1 | 22.0 ± 2.3 |
| Control | 0 | 21.3 ± 1.4 |
| Compound 14 | 0.3 | **24.5 ± 2.0 |
| | 0.1 | 22.0 ± 1.6 |
| Control | 0 | 19.4 ± 1.3 |
| Compound 15 | 0.3 | **22.4 ± 2.0 |
| | 0.1 | 19.9 ± 1.9 |
| Control | 0 | 21.3 ± 1.2 |
| Compound 16 | 3 | *22.5 ± 1.4 |
| | 1 | 21.5 ± 1.4 |
| Control | 0 | 21.4 ± 1.4 |
| Compound 17 | 0.1 | *23.4 ± 2.1 |
| | 0.03 | 22.9 ± 2.5 |
| Control | 0 | 22.3 ± 1.7 |
| Compound 18 | 3 | **25.5 ± 2.5 |
| | 1 | 23.6 ± 2.1 |
| Control | 0 | 20.6 ± 2.1 |
| Compound 19 | 10 | 21.9 ± 1.5 |
| | 3 | 21.8 ± 0.9 |
| Control | 0 | 18.1 ± 1.7 |
| Compound 20 | 10 | **20.5 ± 1.8 |
| Control | 0 | 20.6 ± 2.1 |
| Compound 21 | 10 | **22.6 ± 1.4 |
| Control | 0 | 22.2 ± 1.5 |
| Compound 22 | 1 | **23.8 ± 2.0 |
| | 0.3 | 23.4 ± 2.3 |
| Control | 0 | 22.2 ± 1.5 |
| Compound 23 | 1 | **23.8 ± 1.4 |
| | 0.3 | 22.5 ± 1.9 |
| Control | 0 | 20.2 ± 1.2 |
| Compound 24 | 0.3 | 21.0 ± 1.4 |
| Control | 0 | 21.4 ± 1.4 |
| Compound 25 | 1.0 | *23.6 ± 2.4 |
| Control | 0 | 21.6 ± 2.1 |
| Compound 26 | 1.0 | 22.6 ± 2.3 |
| Control | 0 | 20.3 ± 1.9 |
| Compound 27 | 0.3 | **24.1 ± 1.9 |
| Control | 0 | 22.1 ± 1.8 |
| Compound 18 | 1 | **25.3 ± 2.3 |
| | 0.3 | 22.7 ± 1.6 |
| Control | 0 | 21.2 ± 1.5 |
| Compound 14 | 1 | **23.9 ± 1.8 |
| | 0.3 | 22.0 ± 2.3 |
| Control | 0 | 20.6 ± 1.6 |
| Compound 19 | 3 | **22.8 ± 1.6 |
| | 1 | 20.9 ± 1.8 |
| Control | 0 | 20.2 ± 2.1 |
| Compound 21 | 3 | *21.9 ± 1.8 |

-continued

| | Dose (mg/kg, s.c.) | Duration of Gasping (sec.) Mean ± S.D. |
|---|---|---|
| | 1 | 22.0 ± 1.4 | t-test: **P < 0.01  *0.05 < P < 0.01

Compound 4: 13,14-dihydro-15-keto-16,16-difluoro-PGE$_2$ methyl ester
Compound 5: 13,14-dihydro-15-keto-16,16-difluoro-20-methyl-PGE$_2$
Compound 6: 13,14-dihydro-15-keto-16,16-difluoro-20-methyl-PGE$_2$ methyl ester
Compound 7: 13,14-dihydro-15-keto-20-ethyl-16,16-difluoro-PGE$_2$ methyl ester
Compound 8: 13,14-dihydro-15-keto-20-ethyl-16,16-difluoro-PGE$_2$
Compound 9: 13,14-dihydro-6,15-diketo-5R,S-fluoro-PGE$_2$ methyl ester
Compound 10: 13,14-dihydro-15-keto-17R,S-fluoro-PGE$_2$ methyl ester
Compound 11: 13,14-dihydro-15-keto-16,16-difluoro-PGE$_2$ isopropyl ester
Compound 12: 13,14-dihydro-15-keto-16,16-difluoro-19-desmethyl-PGE$_2$ methyl ester
Compound 13: 13,14-dihydro-15-keto-16,16-difluoro-19-desmethyl-PGE$_2$
Compound 14: 13,14-dihydro-15-keto-16,16-difluoro-PGE$_1$ methyl ester
Compound 15: 13,14-dihydro-6,15-diketo-5,5-difluoro-PGE$_1$ methyl ester
Compound 16: 13,14-dihydro-15-keto-11-dehydroxy-11-methyl-16R,S-fluoro-PGE$_2$ methyl ester
Compound 17: 15-keto-16R,S-fluoro-PGE$_2$
Compound 18: 13,14-dihydro-15-keto-16R,S-fluoro-PGE$_1$
Compound 19: 13,14-dihydro-15-keto-20-ethyl-PGD$_2$ isopropyl
Compound 20: 13,14-dihydro-15-keto-16R,S-fluoro-PGF$_{2\alpha}$ methyl ester
Compound 21: 13,14-dihydro-15-keto-20-ethyl-PGF$_{2\alpha}$ isopropyl ester
Compound 22: 13,14-dihydro-15-keto-16,16-difluoro-6,6a-dehydro-6a-carba-PGI$_1$ methyl ester [13,14-dihydro-15-keto-16,16-difluoro-9(O)-methano-$\Delta^{6(9\alpha)}$-PGI$_1$ methyl ester]
Compound 23: 15-keto-16,16-difluoro-6a-carba-PGI$_2$ [15-ketone-16,16-difluoro-9(O)-methano-PGI$_2$]
Compound 24: 13,14-dihydro-6,15-diketo-16,16-difluoro-PGE$_1$ methyl ester
Compound 25: 13,14-dihydro-15-keto-16,16-difluoro-PGE$_1$ isopropyl ester
Compound 26: 13,14-dihydro-15-keto-16,16-difluoro-PGD$_2$ methyl ester
Compound 27: 13,14-dihydro-15-keto-16,16-difluoro-PGE$_1$ The above results indicate that the duration of gasping was elongated by administration of Compound 4–Compound 27.

Test Example 5

Preparation of encephalo-ischemic animals

Male ddY mice (5 weeks old) were fixed in the dorsal position under the pentobarbital-Na anesthesia. Cervical part was opened along the median line. Bilateral common carotid arteries were exposed and exfoliated taking care not to injure vagus nerves going side by side. A common carotid artery was hanged with a stich and both ends of the stich were passed through a polyethylene tube (inner diameter: 0.5 mm; length: 5 mm) and knotted. The other common carotid artery was treated in the same manner.

Hemostasis was effected by pulling sightly the stich and drawing the artery into the polyethylene tube to narrow the artery. The tube was fixed by an artery-clamp in order to prevent moving of the tube. One common carotid artery was blocked as above and, after 30 seconds, the other common carotid artery was blocked in the same manner. After 10 minutes, the artery-clamps were removed, the knots were cut off and the tubes were removed to restart blood stream.

One-trial passive avoidance-learning experiment

An avoidance-learning machine was composed of an acyl-resin floor (25 cm × 25 cm) having a metal grid extending over the floor and a wooden platform (4.5 cm length × 4.5 cm breath × 3.0 cm height) placed on the grid. After 24 hours from the operation, the animal was placed on the platform and when the animal stepped down the platform, an electric current (0.6 mA, 60 Hz) was applied to the grid for 2 seconds starting from the time immediately after the stepping-down of the animal, as a learning-acquiring trial. After ten minutes, the animal was treated by the encephalo-ischemic procedure. After additional 24 hours, the animal was placed again on the platform and the step-down latency (i.e. time till the animal steps down the platform) was measured up to 300 seconds as an indicative for the passive avoidance-learning behavior acquisition. Test compounds were administered 10 minutes before the acquiring trial.

Grouping was as follows.

| Group | | Administration | Number of Animals |
|---|---|---|---|
| 1 | Normal Control | s.c. | 22 |
| 2 | Ischemic Control | s.c. | 21 |
| 3 | Compound 2  1 μg/kg | s.c. | 20 |
| 4 | "  10 μg/kg | s.c. | 19 |
| 5 | "  100 μg/kg | s.c. | 20 |
| 6 | Compound 27  1 μg/kg | s.c. | 21 |
| 7 | "  10 μg/kg | s.c. | 20 |
| 8 | "  100 μg/kg | s.c. | 21 |

The results are shown in the following Table.

| Group | Step down latency (sec.) Mean ± SE |
|---|---|
| 1 | 274.0 ± 13.8 |
| 2 | ++97.0 ± 15.3 |
| 3 | 124.6 ± 23.5 |
| 4 | 137.8 ± 27.0 |
| 5 | **183.2 ± 25.8 |
| 6 | 130.6 ± 22.7 |
| 7 | 135.1 ± 24.9 |
| 8 | **177.9 ± 24.8 |

++P < 0.01 vs Group 1
**P < 0.01 vs Group 2

In the following data, NMR spectra were measured in $CDCl_3$ using HITACHI R-90H and mass spectra were measured by EI method at an ionization potential of 70 eV using HITACHI M-80B.

* 13,14-dihydro-15-keto-16,16-difluoro-$PGE_2$ $^1H$ NMR ($CDCl_3$) δ 0.93(t,3H,J=7.5 Hz), 1.20–2.70(m,2H), 4.20 (m,1H), 5.40(m,2H)

MS (DI—EI) m/z 388($M^+$), 370($M^+$—$H_2O$), 352($M^+$—$2H_2O$)

* 13,14-dihydro-15-keto-16,16-difluoro-$PGE_1$ isopropyl ester $^1H$ NMR ($CDCl_3$) δ 0.93(t,3H,J=7.5 Hz), 1.23(d,J=7.5 Hz), 1.20–2.70(m,26H), 3.15(s,1H), 4.18(m,1H), 5.00(ht,1H,J=7.5 Hz)

MS (DI—EI) m/z 432($M^+$), 414($M^+$—$H_2O$)

* 13,14-dihydro-15-keto-16,16-difluoro-$PGE_2$ isopropyl ester $^1H$ NMR ($CDCl_3$) δ 0.93(t,3H,J=7.5 Hz), 1.23(d,6H,J=7.5 Hz), 1.30–2.70(m,22H), 2.78( ,1H), 4.20(m,1H), 5.00(ht,1H,J=7.5 Hz)

MS (DI—EI) m/z 430($M^+$), 412($M^+$—$H_2O$)

* 13,14-dihydro-15-keto-16,16-difluoro-19-desmethyl-$PGE_2$ methyl ester $^1H$ NMR ($CDCl_3$) δ 0.98(t,3H,J=7.5 Hz), 1.50–2.70(m,20H), 2.94 (s,1H), 3.68(s,3H), 4.20(m,1H), 5.40(m,2H)

MS (DI—EI) m/z 388($M^+$), 370($M^+$—$H_2O$), 357($M^+$—$H_2O$—$CH_3O$), 355($M^+$—$H_2O$—$CH_3$)

* 13,14-dihydro-15-keto-16,16-difluoro-19-desmethyl-$PGE_2$ $^1H$ NMR ($CDCl_3$) δ 0.98(t,3H,J=7.5 Hz), 1.40–2.70(m,22H), 4.20 (m,1H), 5.40(m,2H)

MS (DI—EI) m/z 374($M^+$), 356($M^+$—$H_2O$), 338($M^+$—$2H_2O$)

* 13,14-dihydro-15-keto-16,16-difluoro-11-dehydroxy-11-methyl-$PGE_2$ methyl ester $^1H$ NMR ($CDCl_3$) δ 0.93(t,3H,J=7.5 Hz), 1.14(d,3H,J=6 Hz), 1.25–2.80(m,22H), 3.63(s,3H), 5.38(m,2H)

MS (DI—EI) m/z 400($M^+$) 369($M^+$—$CH_3O$)

* 13,14-dihydro-15-keto-16,16-difluoro-$PGD_2$ methyl ester $^1H$ NMR ($CDCl_3$) δ 0.91(t,3H,J=7.5 Hz), 1.20–3.20(m,23H), 3.68 (s,3H), 4.44(m,1H,J=1.2 Hz), 5.49(m,2H)

MS (DI—EI) m/z 402($M^+$), 384($M^+$—$H_2O$), 353($M^+$—$H_2O$—$CH_3O$)

* 13,14-dihydro-15-keto-16,16-difluoro-20-methyl-$PGE_2$ methyl ester $^1$NMR ($CDCl_3$) δ 0.90(t,3H,J=7.5 Hz), 1.20–2.70(m,26H), 4.20 (m,1H), 5.41(m,2H)

MS (DI—EI) m/z 402($M^+$) 384($M^+$—$H_2O$), 366($M^+$—$2H_2O$)

* 13,14-dihydro-15-keto-16,16-difluoro-20-ethyl-$PGE_2$ methyl ester $^1H$ NMR ($CDCl_3$) δ 0.89(t,3H,J=7.5 Hz), 1.20–2.70(m,26H), 2.93 (s,1H), 3.68(s,3H), 4.20(m,1H), 5.41(m,2H)

MS (DI—EI) m/z 430($M^+$), 412($M^+$—$H_2O$), 399($M^+$—$CH_3O$), 381($M^+$—$H_2O$—$CH_3O$)

* 13,14-dihydro-15-keto-16,16-difluoro-20-ethyl-$PGE_2$ $^1H$ NMR ($CDCl_3$) δ 0.94(t,3H,J=7.5 Hz), 1.20–2.70(m,27H), 4.21 (m,1H), 5.43(m,2H)

MS (DI—EI) m/z 416($M^+$), 398($M^+$—$H_2O$), 380($M^+$—$2H_2O$)

What is claimed is:

1. A method of treatment for improving a deterioration of encephalic function caused by a condition comprising or associated with ischemic lesion, hemorrhagic lesion, local or propagated pressure lesion due to edema or hydrocephalia or a disorder of cerebral metabolism secondarily induced by a disorder of cerebral circulation kinetics which comprises administering, to a subject in need of such treatment, a 15-keto-prostaglandin compound of the formulae (I) or (II)

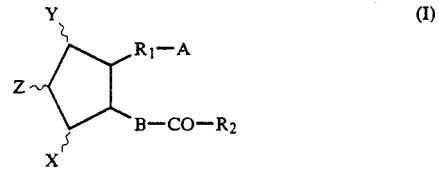

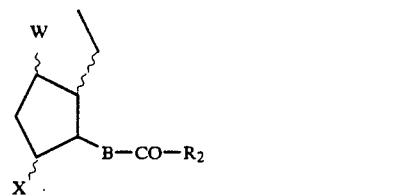

wherein X and Y are hydrogen, hydroxy, halo, lower alkyl, hydroxy(lower)alkyl, or oxo with a proviso that in formula (I) at least one of X and Y is other than hydrogen and the five-membered ring may have at least one double bond, Z is hydrogen or halo, A is —$CH_2OH$, —$COCH_2OH$, —COOH or a salt, an ester or an amide of —COOH, B is —$CH_2$—$CH_2$—, —CH=CH— or —C≡C—, W is oxygen atom or carbon atom, $R_1$ is a bivalent saturated or unsaturated, lower or medium aliphatic hydrocarbon residue, which is unsubstituted or substituted with halogen, oxo, phenyl, tolyl, xylyl or thienyl, $R_2$ is saturated or unsaturated, lower or medium aliphatic hydrocarbon residue which is unsubstituted or substituted with halo, hydroxy, oxo, lower alkoxy, lower alkanoyloxy, cyclo(lower)-alkyl, aryl or aryloxy and wherein in $R_2$ aryl and aryl of aryloxy are independently phenyl, tolyl, xylyl or thienyl, in an amount effective for improvement of encephalic function.

2. The method according to claim 1, wherein said 15-keto-prostaglandin compound is a 16-mono- or di-halo-15-keto-prostaglandin compound.

3. The method according to claim 1, wherein said 15-keto-prostaglandin compound is a 13,14-dihydro-16-mono- or di-halo-15-keto-prostaglandin compound.

4. The method according to claim 1, wherein said 15-keto-prostaglandin compound is a 13,14-dihydro-16-mono- or di-fluoro-15-keto-prostaglandin compound.

5. The method according to claim 1, wherein said 15-keto-prostaglandin compound is a 6,15-diketo-prostaglandin compound.

6. The method according to claim 1, wherein said 15-keto-prostaglandin compound is a 13,14-dihydro-6,15-diketo-prostaglandin compound.

7. The method according to claim 1, wherein said 15-keto-prostaglandin compound is a 15-keto-19-alkyl-prostaglandin compound.

8. The method according to claim 1, wherein said 15-keto-prostaglandin compound is a 13,14-dihydro-15-keto-19-alkyl-prostaglandin compound.

9. The method according to claim 1, wherein said 15-keto-prostaglandin compound is a 13,14-dihydro-15-keto-19-methyl-prostaglandin compound.

10. The method according to claim 1, wherein said 15-keto-prostaglandin compound is a 13,14-dihydro-6,15-diketo-5-mono or di-halo-prostaglandin compound.

11. The method according to claim 1, wherein said 15-keto-prostaglandin compound is a 15-keto-prostaglandin I compound.

12. A method of treatment for improving a deterioration of encephalic function caused by a condition comprising or associated with ischemic lesion, hemorrhagic lesion, local or propagated pressure lesion due to edema or hydrocephalia or a disorder of cerebral metabolism secondarily induced by a disorder of cerebral circulation kinetics which comprises administering, to a subject in need of such treatment, a compound of the formula:

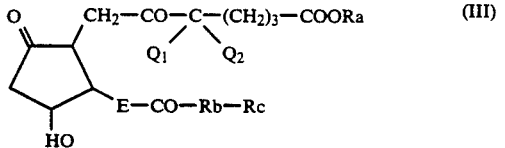

wherein $Q_1$ is halogen, $Q_2$ is hydrogen or halogen, E is —$CH_2$—$CH_2$— or —CH=CH—, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, phenyl which is unsubstituted or substituted with halogen or halo(lower)alkyl, or phenoxy which is unsubstituted or substituted with halogen or halo(lower) alkyl or a pharmaceutically acceptable salt in case of Ra is hydrogen, with the proviso that when Rc is phenoxy, Rb is lower alkylene.

13. The method according to claim 12, in which $Q_1$ is fluorine.

14. The method according to claim 12, in which E is —$CH_2$—$CH_2$—.

15. The method according to claim 12, in which Rb is single bond and Rc is lower alkyl.

16. The method according to claim 1, wherein said compound is administered to provide an encephalic metabolism activating action.

17. The method according to claim 1, wherein said compound is a compound of formula (I) and is administered to provide an encephalic function protecting action.

18. The method according to claim 1, wherein the compound is a compound of formula (I) and is administered to improve encephalic circulation.

19. The method according to claim 1, wherein the compound is a compound of formula (I) and is administered to a subject experiencing encephalic ischemia.

20. The method according to claim 12, wherein said compound is administered to provide an encephalic metabolism activating action.

21. The method according to claim 12, wherein said compound is administered to provide an encephalic function protecting action.

22. The method according to claim 12, wherein the compound is administered to improve encephalic circulation.

23. The method according to claim 12, wherein the compound is administered to a subject experiencing encephalic ischemia.

24. A method of inhibiting cerebrovascular contraction which comprises administering, to a subject in need of such treatment, a compound of formula (I)

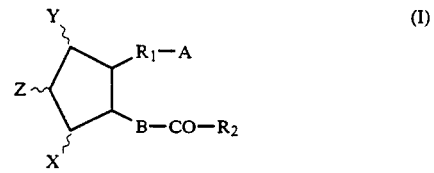

wherein X and Y are hydrogen, hydroxy, halo, lower alkyl, hydroxy(lower)alkyl, or oxo with the proviso that at least one of X and Y is other than hydrogen and the five-membered ring may have at least one double bond, Z is hydrogen or halo, A is —$CH_2OH$, —$COCH_2OH$, —COOH or a salt, an ester or an amide of —COOH, B is —$CH_2$—$CH_2$—, —CH=CH— or —C≡C—, $R_1$ is bivalent saturated or unsaturated, lower or medium aliphatic hydrocarbon residue, which is unsubstituted or substituted with halogen, oxo, phenyl, tolyl, xylyl or thienyl, $R_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy and wherein in $R_2$ aryl and aryl of aryloxy are independently phenyl, tolyl, xylyl or thienyl, in an amount effective for inhibition of cerebrovascular contraction.

25. A method for improving learning and memory which comprises administering to a subject in need of such improvement a compound of formula (I)

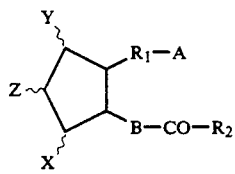

wherein X and Y are hydrogen, hydroxy, halo, lower alkyl, hydroxy(lower)alkyl, or oxo with the proviso that at least one of X and Y is other than hydrogen and the five-membered ring may have at least one double bond, Z is hydrogen or halo, A is —CH$_2$OH, —COCH$_2$OH, —COOH or a salt, an ester or an amide of —COOH, B is —CH$_2$—CH$_2$—, —CH=CH— or —C≡C—, R$_1$ is bivalent saturated or unsaturated, lower or medium aliphatic hydrocarbon residue, which is unsubstituted or substituted with halogen, oxo, phenyl, tolyl, xylyl or thienyl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy and wherein in R$_2$ aryl and aryl of aryloxy are independently phenyl, tolyl, xylyl or thienyl, in an amount effective for improving said learning and memory.

26. The method according to claim 24, wherein the compound of the formula (I) is a compound of the formula (III)

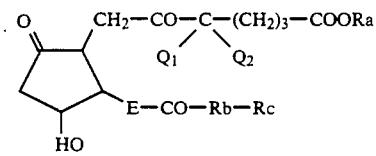

wherein Q$_1$ is halogen, Q$_2$ is hydrogen or halogen, E is —CH$_2$—CH$_2$— or —CH=CH—, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, phenyl which is unsubstituted or substituted with halogen or halo(lower)alkyl, or phenoxy which is unsubstituted or substituted with halogen or halo(lower) alkyl or a pharmaceutically acceptable salt in case of Ra is hydrogen.

27. The method of claim 25, wherein the compound of the formula (I) is a compound of the formula (III)

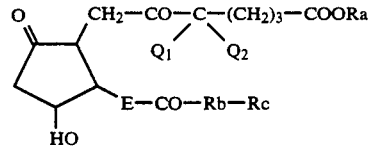

wherein Q$_1$ is halogen, Q$_2$ is hydrogen or halogen, E is —CH$_2$—CH$_2$— or —CH=CH—, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, phenyl which is unsubstituted or substituted with halogen or halo(lower) alkyl, or phenoxy which is unsubstituted or substituted with halogen or halo(lower) alkyl or a pharmaceutically acceptable salt in case of Ra is hydrogen.

28. A method of treatment for improving a deterioration of encephalic function caused by ischemia which comprises administering to a subject in need of such treatment, a 15-keto-prostaglandin compound of the formulae (I) or (II)

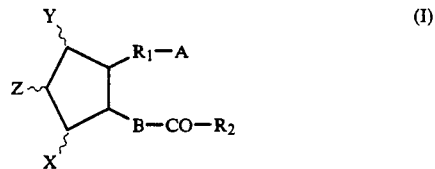

wherein X and Y are hydrogen, hydroxy, halo, lower alkyl, hydroxy(lower)alkyl, or oxo with a proviso that in formula (I) at least one of X and Y is other than hydrogen and the five-membered ring may have at least one double bond, Z is hydrogen or halo, A is —CH$_2$OH, —COCH$_2$OH, —COOH or a salt, an ester or an amide of —COOH, B is —CH$_2$—CH$_2$—, —CH=CH— or —C≡C—, W is oxygen atom or carbon atom, R$_1$ is a bivalent saturated or unsaturated, lower or medium aliphatic hydrocarbon residue, which is unsubstituted or substituted with halogen, oxo, phenyl, tolyl, xylyl or thienyl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)-alkyl, aryl or aryloxy and wherein in R$_2$ aryl and aryl of aryloxy are independently phenyl, tolyl, xylyl or thienyl, in an amount effective for improvement of encephalic function.

29. A method of treatment for improving a deterioration of encephalic function caused by hypoxia which comprises administering to a subject in need of such treatment, a 15-keto-prostaglandin compound of the formulae (I) or (II)

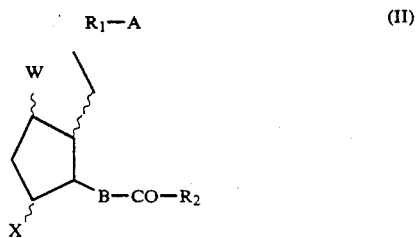

wherein X and Y are hydrogen, hydroxy, halo, lower alkyl, hydroxy(lower)alkyl, or oxo with a proviso that in formula (I) at least one of X and Y is other than hydrogen and the five-membered ring may have at least one double bond, Z is hydrogen or halo, A is —CH$_2$OH, —COCH$_2$OH, —COOH or a salt, an ester or an amide of —COOH, B is —CH$_2$—CH$_2$—, —CH=CH— or —C≡C—, W is oxygen atom or carbon atom, R$_1$ is a bivalent saturated or unsaturated, lower or medium aliphatic hydrocarbon residue, which is unsubstituted or substituted with halogen, oxo, phenyl, tolyl, xylyl or thienyl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)-alkyl, aryl or aryloxy and wherein in R$_2$ aryl and aryl of aryloxy are independently phenyl, tolyl, xylyl or thienyl, in an amount effective for improvement of encephalic function.

30. A method of treatment for improving a deterioration of encephalic function caused by hypoxia which comprises administering to a subject in need of such treatment, a compound of the formula (III)

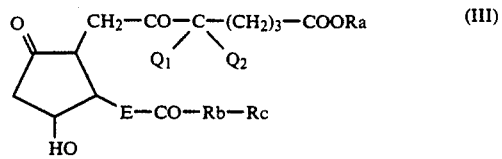

wherein Q$_1$ is halogen, Q$_2$ is hydrogen or halogen, E is —CH$_2$—CH$_2$— or —CH=CH—, Ra is hydrogen or lower alkyl, Rb is single bond or lower alkylene, and Rc is lower alkyl which is unsubstituted or substituted with halogen, lower cycloalkyl which is unsubstituted or substituted with lower alkyl, phenyl which is unsubstituted or substituted with halogen or halo(lower)alkyl, or phenoxy which is unsubstituted or substituted with halogen or halo(lower)alkyl or a pharmaceutically acceptable salt in case of Ra is hydrogen, with the proviso that when Rc is phenoxy, Rb is lower alkylene, in an amount effective for improvement of encephalic function.

* * * * *